US012006351B2

(12) United States Patent
Bourboulia et al.

(10) Patent No.: US 12,006,351 B2
(45) Date of Patent: Jun. 11, 2024

(54) COMPOSITIONS AND METHODS FOR MODIFYING ACTIVITY OF EXTRACELLULAR MMP-2

(71) Applicant: THE RESEARCH FOUNDATION FOR THE STATE UNIVERSITY OF NEW YORK, Syracuse, NY (US)

(72) Inventors: Dimitra Bourboulia, Fayetteville, NY (US); Mehdi Mollapour, Syracuse, NY (US); Gennady Bratslavsky, Syracuse, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 503 days.

(21) Appl. No.: 16/314,227

(22) PCT Filed: Jun. 30, 2017

(86) PCT No.: PCT/US2017/040442
§ 371 (c)(1),
(2) Date: Dec. 28, 2018

(87) PCT Pub. No.: WO2018/006049
PCT Pub. Date: Jan. 4, 2018

(65) Prior Publication Data
US 2019/0322724 A1 Oct. 24, 2019

Related U.S. Application Data

(60) Provisional application No. 62/356,797, filed on Jun. 30, 2016.

(51) Int. Cl.
| C07K 14/81 | (2006.01) |
| A61K 38/57 | (2006.01) |
| A61K 39/395 | (2006.01) |
| C07K 16/32 | (2006.01) |
| C07K 16/40 | (2006.01) |
| A61K 38/00 | (2006.01) |

(52) U.S. Cl.
CPC .......... *C07K 14/8146* (2013.01); *A61K 38/57* (2013.01); *A61K 39/3955* (2013.01); *C07K 16/32* (2013.01); *C07K 16/40* (2013.01); *A61K 38/00* (2013.01); *C07K 2317/76* (2013.01)

(58) Field of Classification Search
None
See application file for complete search history.

(56) References Cited

U.S. PATENT DOCUMENTS

| 6,022,948 | A | 2/2000 | Goldberg |
| 6,534,635 | B1 * | 3/2003 | Miyazaki ............ A61P 35/04 530/402 |
| 7,060,795 | B2 * | 6/2006 | Quirk .................. A61P 17/02 530/350 |
| 2004/0261142 | A1 | 12/2004 | Yeatman et al. |
| 2006/0099684 | A1 | 5/2006 | Moses et al. |
| 2009/0318342 | A1 | 12/2009 | Nagase et al. |
| 2013/0030034 | A9 | 1/2013 | Niitsu et al. |
| 2016/0297893 | A1 * | 10/2016 | Vijayendran ........ G01N 33/577 |

OTHER PUBLICATIONS

Williamson et al., Journal of Biological Chemistry, vol. 276, No. 35, Issue of Aug. 31, pp. 32966-32970, 2001.*
UniProtKB/Swiss-Prot Assession No. P16035, Nov. 11, 2015, 5 pages. http://www.uniprot.org/uniprot/P16035.txt?version=168.
Caterina, J.J., et al., Inactivating Mutation of the Mouse Tissue Inhibitor of Metalloproteinases-2(Timp-2) Gene Alters ProMMP-2 Activation, J. Biol. Chem., Aug. 25, 2000, vol. 275, No. 34., pp. 26416-26422.

* cited by examiner

*Primary Examiner* — Marianne P Allen
(74) *Attorney, Agent, or Firm* — Peter Fallon; Lance Reich

(57) ABSTRACT

Provided are compositions and methods for inhibiting extracellular matrix metalloproteinase-2 (MMP-2) activity. Inhibition of extracellular MMP-2 activity can be useful for restricting extracellular matrix remodeling, tumor cell migration, cell invasion, and/or metastasis. The compositions comprise mutants of Tissue Inhibitor of Metalloproteinase-2 (TIMP-2), where the tyrosine at position 62, 90 and/or 165 has been substituted with a non-phosphorylatable amino acid or with a phosphomimetic of phosphorylated tyrosine, and/or anti-Src antibodies. The method comprises delivering to an extracellular region of a tissue, a composition comprising a TIMP-2 mutant and/or an anti-Src antibody.

8 Claims, 12 Drawing Sheets
Specification includes a Sequence Listing.

Figure 2
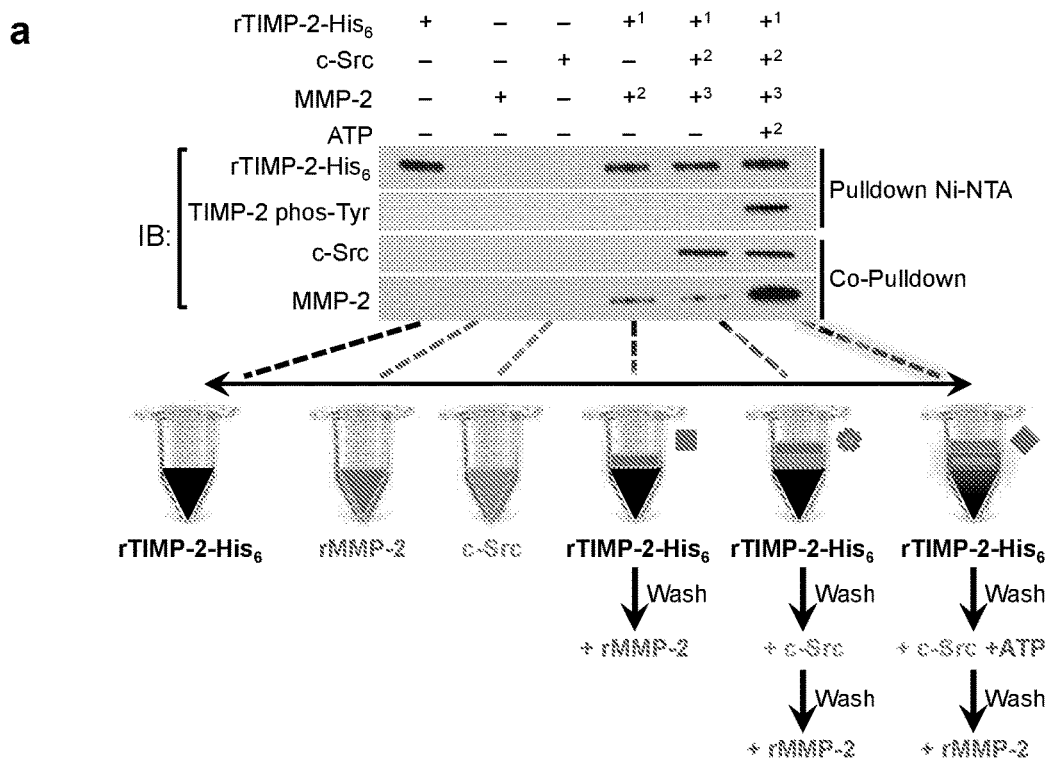
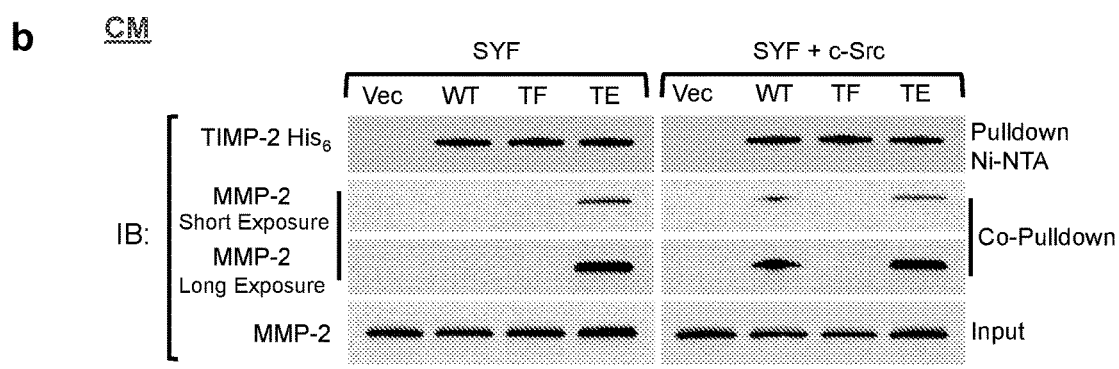
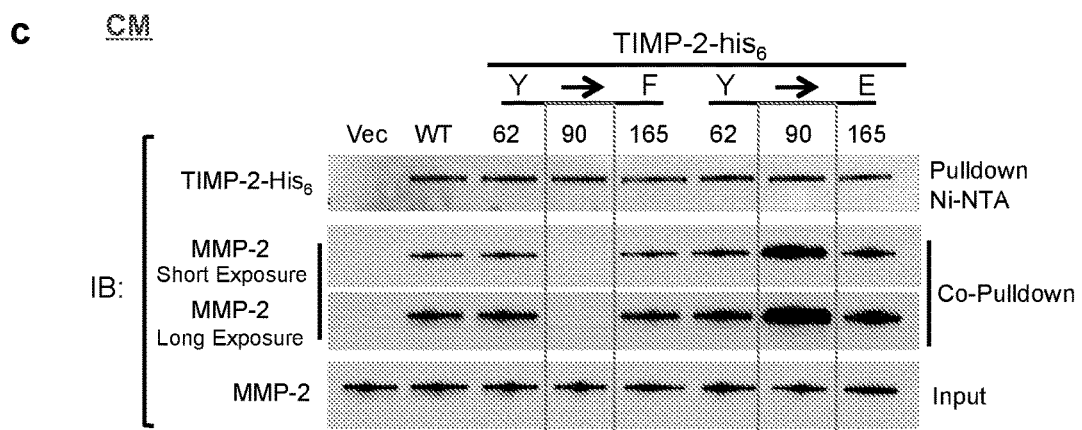

Figure 3 (continued)
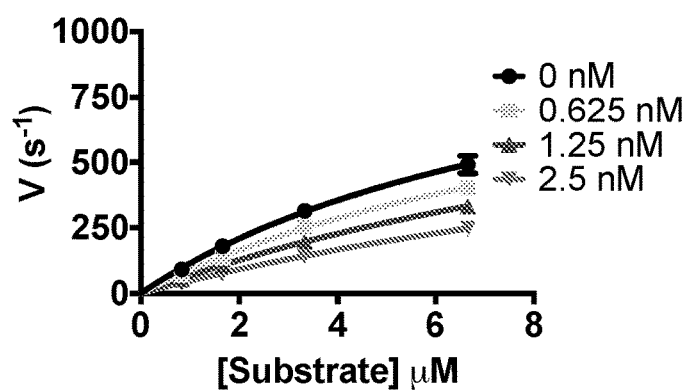
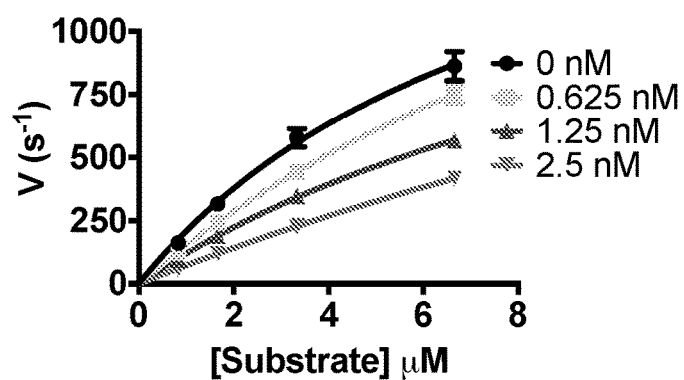
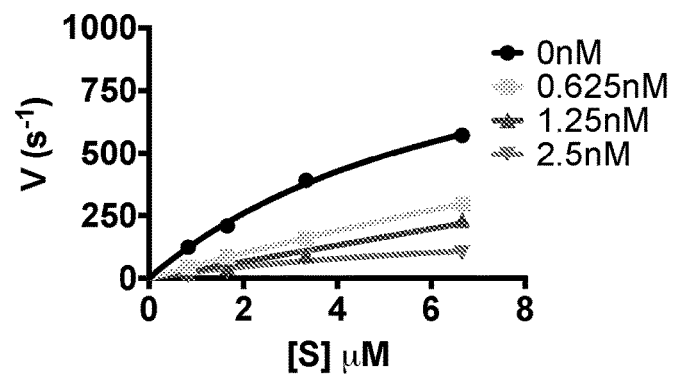

Figure 5
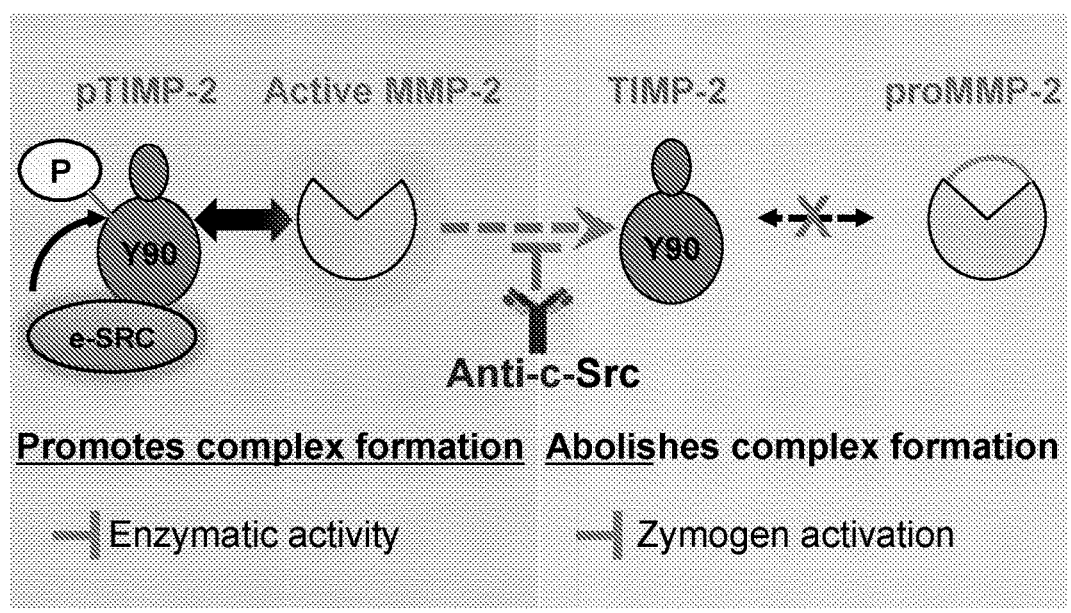
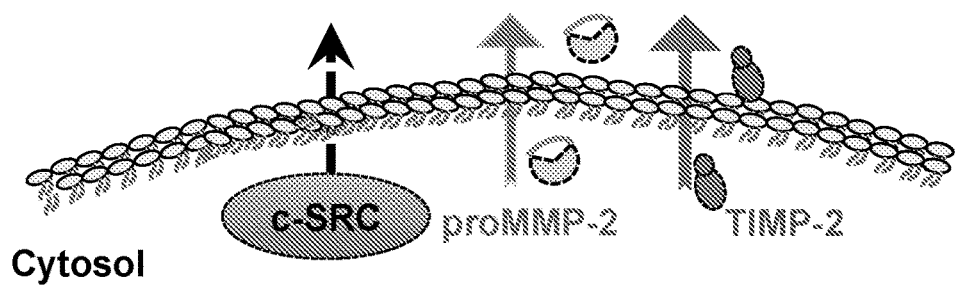

Figure 6 a

Signal peptide (TIMP-2, aa 1-26) ←——————————→ *N-term* - - - - →

```
TIMP-1  MAPFE----PLASGILLLLWLIAPSR----ACTCVPPHPQTAFCNSDLVIRAKFVGTPEVNQ   54
TIMP-2  MGAAARTLRLALGLLLLATLLRP----ADACSCSPVHPQQAFCNADVVIRAKAVSEKEVDS   57
TIMP-3  M--------TPWLGLIVLLGSWSLGDWG-AEACTCSPSHPQDAFCNSDIVIRAKVVGKKLVKE  54
TIMP-4  MPGSPRPAPSWVLLLRLLALLRPPGLGEACSCAPAHPQQHICHSALVIRAKISSEKVVPA   60
             *         *       **   * ***    *    *****      *
                Y62                               Y90
TIMP-1  TT--------LYQRYEIKMTKMYKGFQALGDAADIRFVYTPAMESVCGYFHRSHNRSEEFL  107
TIMP-2  GNDIYGNPIKRIQYEIKQIKMFKG--PE----KDIEFIYTAPSSAVCGVSLDV-GGKKEYL  111
TIMP-3  G--------PFGTLVYTIKQMKMYRGFTKM----PHVQYIHTEASESLCGLKLEV-N-KYQYL  103
TIMP-4  SADP-ADTEKMLRYEIKQIKMFKGFEKV----KDVQYIYTPFDSSLCGVKLEA-NSQKQYL  115
              * **  **  *                *    **C-term       *
                                                     Y165 →
TIMP-1  IAGKLQ-DGLLHITTCSFVAPWNSLSLAQRRGFTKTYTVGCEECTVFPCLSIPCKLQSGT  166
TIMP-2  IAGKAEGDGKMHITLCDFIVPWDTLSTTQKKSLNHRYQMGCE-CKITRCPMIPCYISSPD  170
TIMP-3  LTGRVY-DGKMYTGLCNFVERWDQLTLSQRKGLNYRYHLGCN-CKIKSCYYLPCFVTSKN  161
TIMP-4  LTGQVLSDGKVFIHLCNYIEPWEDLSLVQRESLNHRYHLNCG-CQITTCYTVPCTISAPN  174
          **     **  *  *  *   *     *    *   *       *  *   **

TIMP-1  HCLWTDQLLQGSEKGFQSRHLACLPREPGLCTWQSLRSQIA-------------------  207
TIMP-2  ECLWMDWVTEKNINGHQAKFFACIKRSDGSCAWYRGAAPPKQEFLDIEDP           220
TIMP-3  ECLWTDMLSNFGYPGYQSKHYACIROKGGYCSWYRGWAPPDKSIINATDP           211
TIMP-4  ECLWTDWLLERKLYGYQAQHYVCMKHVDGTCSWYRGHLPLRKEFVDIVQP           224
         ***  *       *       *     *  *
``` b

Extracts

|  | WT | Y62F Y90F | Y62F Y165F | Y90F Y165F | TF |
|---|---|---|---|---|---|
| IB: TIMP-2 His₆ | | | | | | Pulldown Ni-NTA |
| phos-Tyr | | | | | | Short Exposure |
| | | | | | | Long Exposure | c

Extracts

SYF | SYF + c-Src
Vec WT TF | Vec WT TF

IB: TIMP-2 His₆ — Pulldown Ni-NTA
phos-Tyr — Short Exposure
— Long Exposure

Figure 9
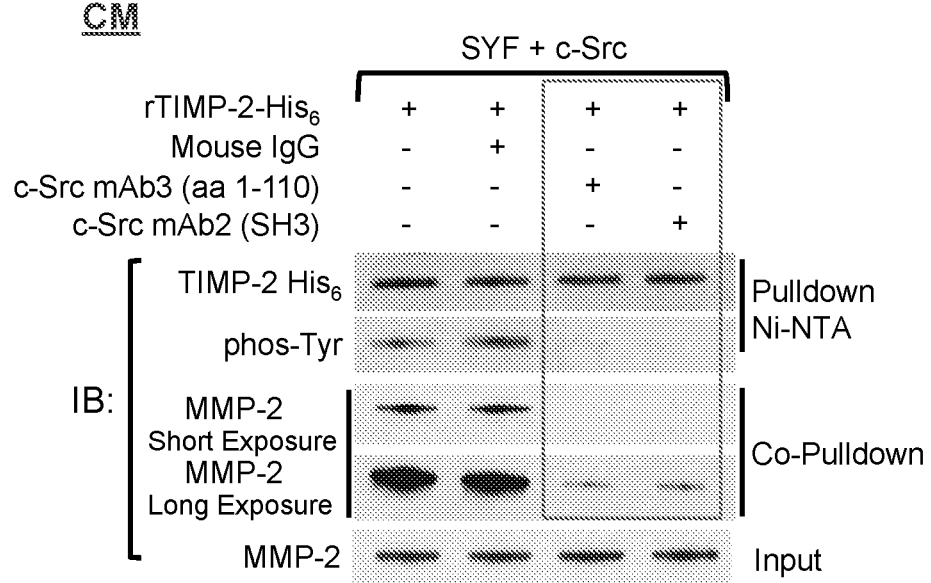
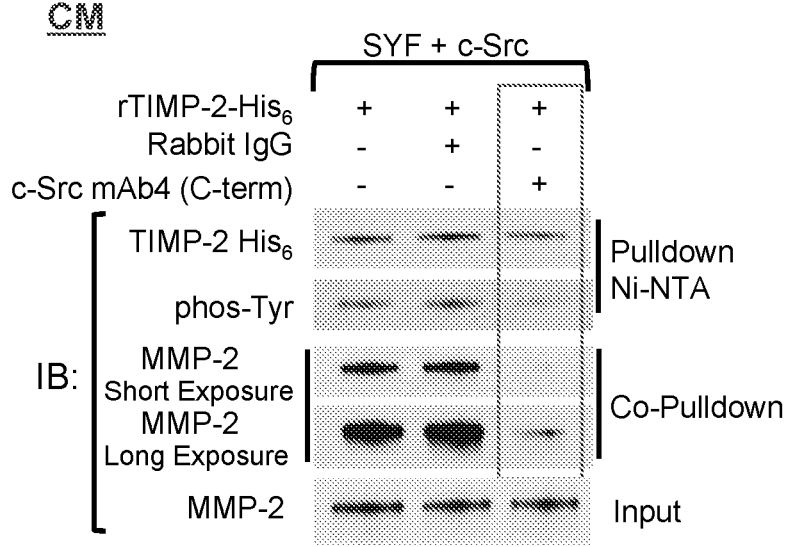

Figure 11
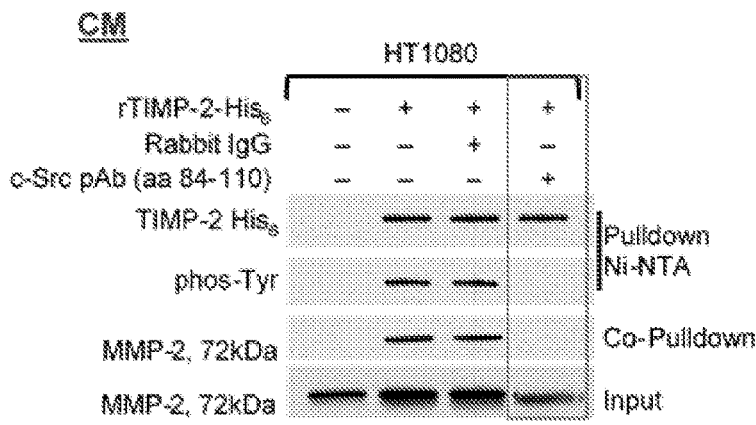
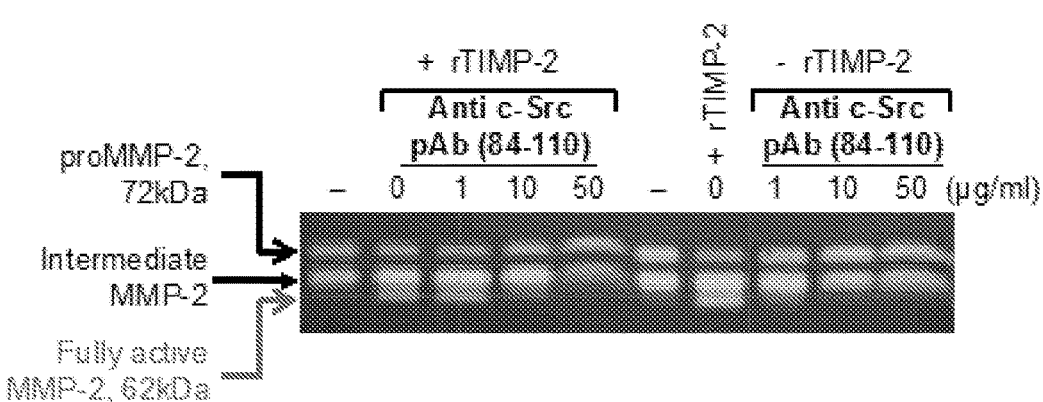
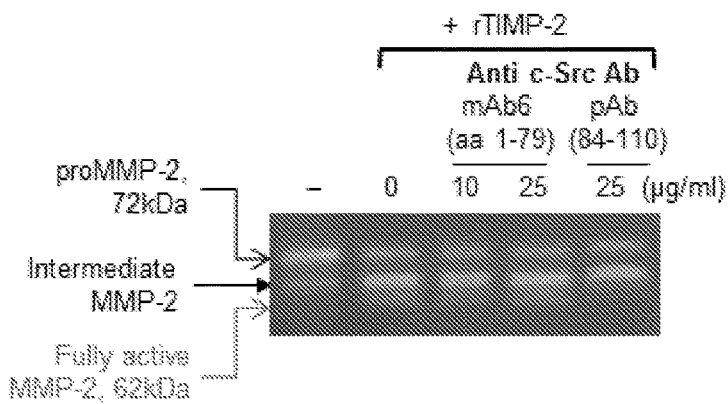

SEQUENCE LISTING

<160> NUMBER OF SEQ ID NOS: 5

<210> SEQ ID NO 1
<211> LENGTH: 220
<212> TYPE: PRT
<213> ORGANISM: human

<400> SEQUENCE: 1

Met Gly Ala Ala Ala Arg Thr Leu Arg Leu Ala Leu Gly Leu Leu Leu
1               5                   10                  15

Leu Ala Thr Leu Leu Arg Pro Ala Asp Ala Cys Ser Cys Ser Pro Val
            20                  25                  30

His Pro Gln Gln Ala Phe Cys Asn Ala Asp Val Val Ile Arg Ala Lys

```
                35                  40                  45
Ala Val Ser Glu Lys Glu Val Asp Ser Gly Asn Asp Ile Tyr Gly Asn
 50                  55                  60

Pro Ile Lys Arg Ile Gln Tyr Glu Ile Lys Gln Ile Lys Met Phe Lys
65                  70                  75                  80

Gly Pro Glu Lys Asp Ile Glu Phe Ile Tyr Thr Ala Pro Ser Ser Ala
                85                  90                  95

Val Cys Gly Val Ser Leu Asp Val Gly Gly Lys Lys Gly Tyr Leu Ile
                100                 105                 110

Ala Gly Lys Ala Glu Gly Asp Gly Lys Met His Ile Thr Leu Cys Asp
                115                 120                 125

Phe Ile Val Pro Trp Asp Thr Leu Ser Thr Thr Gln Lys Lys Ser Leu
                130                 135                 140

Asn His Arg Tyr Gln Met Gly Cys Glu Cys Lys Ile Thr Arg Cys Pro
145                 150                 155                 160

Met Ile Pro Cys Tyr Ile Ser Ser Pro Asp Glu Cys Leu Trp Met Asp
                165                 170                 175

Trp Val Thr Glu Lys Asn Ile Asn Gly His Gln Ala Lys Phe Phe Ala
                180                 185                 190

Cys Ile Lys Arg Ser Asp Gly Ser Cys Ala Trp Tyr Arg Gly Ala Ala
                195                 200                 205

Pro Pro Lys Gln Glu Phe Leu Asp Ile Glu Asp Pro
                210                 215                 220

<210> SEQ ID NO 2
<211> LENGTH: 207
<212> TYPE: PRT
<213> ORGANISM: human

<400> SEQUENCE: 2

Met Ala Pro Phe Glu Pro Leu Ala Ser Gly Ile Leu Leu Leu Leu Trp
1               5                   10                  15

Leu Ile Ala Pro Ser Arg Ala Cys Thr Cys Val Pro Pro His Pro Gln
                20                  25                  30

Thr Ala Phe Cys Asn Ser Asp Leu Val Ile Arg Ala Lys Phe Val Gly
                35                  40                  45

Thr Pro Glu Val Asn Gln Thr Thr Leu Tyr Gln Arg Tyr Glu Ile Lys
 50                  55                  60

Met Thr Lys Met Tyr Lys Gly Phe Gln Ala Leu Gly Asp Ala Ala Asp
65                  70                  75                  80

Ile Arg Phe Val Tyr Thr Pro Ala Met Glu Ser Val Cys Gly Tyr Phe
                85                  90                  95

His Arg Ser His Asn Arg Ser Glu Glu Phe Leu Ile Ala Gly Lys Leu
                100                 105                 110

Gln Asp Gly Leu Leu His Ile Thr Thr Cys Ser Phe Val Ala Pro Trp
                115                 120                 125

Asn Ser Leu Ser Leu Ala Gln Arg Arg Gly Phe Thr Lys Thr Tyr Thr
                130                 135                 140

Val Gly Cys Glu Glu Cys Thr Val Phe Pro Cys Leu Ser Ile Pro Cys
145                 150                 155                 160

Lys Leu Gln Ser Gly Thr His Cys Leu Trp Thr Asp Gln Leu Leu Gln
                165                 170                 175

Gly Ser Glu Lys Gly Phe Gln Ser Arg His Leu Ala Cys Leu Pro Arg
                180                 185                 190
```

```
Glu Pro Gly Leu Cys Thr Trp Gln Ser Leu Arg Ser Gln Ile Ala
            195                 200                 205
```

<210> SEQ ID NO 3
<211> LENGTH: 211
<212> TYPE: PRT
<213> ORGANISM: human

<400> SEQUENCE: 3

```
Met Thr Pro Trp Leu Gly Leu Ile Val Leu Leu Gly Ser Trp Ser Leu
1               5                   10                  15

Gly Asp Trp Gly Ala Glu Ala Cys Thr Cys Ser Pro Ser His Pro Gln
            20                  25                  30

Asp Ala Phe Cys Asn Ser Asp Ile Val Ile Arg Ala Lys Val Val Gly
            35                  40                  45

Lys Lys Leu Val Lys Glu Gly Pro Phe Gly Thr Leu Val Tyr Thr Ile
50                  55                  60

Lys Gln Met Lys Met Tyr Arg Gly Phe Thr Lys Met Pro His Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
            115                 120                 125

Leu Ser Gln Arg Lys Gly Leu Asn Tyr Arg Tyr His Leu Gly Cys Asn
130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
            195                 200                 205

Thr Asp Pro
    210
```

<210> SEQ ID NO 4
<211> LENGTH: 224
<212> TYPE: PRT
<213> ORGANISM: Human

<400> SEQUENCE: 4

```
Met Pro Gly Ser Pro Arg Pro Ala Pro Ser Trp Val Leu Leu Leu Arg
1               5                   10                  15

Leu Leu Ala Leu Leu Arg Pro Pro Gly Leu Gly Glu Ala Cys Ser Cys
            20                  25                  30

Ala Pro Ala His Pro Gln Gln His Ile Cys His Ser Ala Leu Val Ile
            35                  40                  45

Arg Ala Lys Ile Ser Ser Glu Lys Val Val Pro Ala Ser Ala Asp Pro
50                  55                  60

Ala Asp Thr Glu Lys Met Leu Arg Tyr Glu Ile Lys Gln Ile Lys Met
65                  70                  75                  80

Phe Lys Gly Phe Glu Lys Val Lys Asp Val Gln Tyr Ile Tyr Thr Pro
                85                  90                  95
```

```
Phe Asp Ser Ser Leu Cys Gly Val Lys Leu Glu Ala Asn Ser Gln Lys
            100             105             110

Gln Tyr Leu Leu Thr Gly Gln Val Leu Ser Asp Gly Lys Val Phe Ile
        115             120             125

His Leu Cys Asn Tyr Ile Glu Pro Trp Glu Asp Leu Ser Leu Val Gln
        130             135             140

Arg Glu Ser Leu Asn His His Tyr His Leu Asn Cys Gly Cys Gln Ile
145                 150             155                 160

Thr Thr Cys Tyr Thr Val Pro Cys Thr Ile Ser Ala Pro Asn Glu Cys
                165             170             175

Leu Trp Thr Asp Trp Leu Leu Glu Arg Lys Leu Tyr Gly Tyr Gln Ala
            180             185             190

Gln His Tyr Val Cys Met Lys His Val Asp Gly Thr Cys Ser Trp Tyr
        195             200             205

Arg Gly His Leu Pro Leu Arg Lys Glu Phe Val Asp Ile Val Gln Pro
        210             215             220

<210> SEQ ID NO 5
<211> LENGTH: 27
<212> TYPE: PRT
<213> ORGANISM: human

<400> SEQUENCE: 5

Gly Gly Val Thr Thr Phe Val Ala Leu Tyr Asp Tyr Glu Ser Arg Thr
1               5                   10                  15

Glu Thr Asp Leu Ser Phe Lys Lys Gly Glu Arg
            20                  25
```

COMPOSITIONS AND METHODS FOR MODIFYING ACTIVITY OF EXTRACELLULAR MMP-2

CROSS-REFERENCE TO RELATED APPLICATIONS

This application claims priority to U.S. Provisional Application No. 62/356,797, filed on Jun. 30, 2016, the disclosure of which is incorporated herein by reference.

This application contains a Sequence Listing in an ASCII plain text file, which is incorporated herein by reference. The name of text file is 2004-110US01. The text file was created on Oct. 14, 2021, and the size of the text file is 8231 bytes.

BACKGROUND OF THE DISCLOSURE

Changes in extracellular matrix (ECM) and associated cell migration and invasion therethrough are important aspects of many pathological conditions. However, the extracellular events that lead up to ECM remodeling are not completely understood. In its classic form, signal transduction progresses from the outside to the inside of a cell and integrates a series of protein modifications, primarily phosphorylation. While phosphoproteins and, more recently, kinases have been shown to be present in the extracellular space, signal transduction occurring outside the cell through phosphorylation remains undefined.

Recent analysis of the human phosphoproteome suggests that a considerable number of secreted proteins, including Matrix Metalloproteinases (MMPs) and Tissue Inhibitor of Metalloproteinases (TIMPs), contain phosphotyrosine residues. TIMP-2 is a protein that contains an N-terminus 26 amino acid long signal peptide (SP) that directs the protein to the extracellular space through the ER/Golgi apparatus. In the extracellular compartment, TIMP-2 may exist both in a released and/or bound to the cell surface form through receptors. TIMP-2 is known to be a natural inhibitor of MMPs activity, and known facilitator of latent pro-MMP-2 activation. However, the extracellular event that signals for MMP-2:TIMP-2 complex formation is unknown.

SUMMARY OF THE DISCLOSURE

The present disclosure provides compositions and methods useful for inhibiting extracellular MMP-2 activity. Inhibition of extracellular MMP-2 activity can be useful for restricting ECM remodeling, tumor cell migration, cell invasion and metastasis.

This disclosure is based on our findings that mouse and human cells release proto-oncogene non-receptor tyrosine kinase c-Src in the extracellular space. We report that extracellular c-Src phosphorylates TIMP-2 on tyrosines (Tyr, Y) 62, 90 and 165. c-Src-mediated phosphorylation of TIMP-2 is required for complex formation of TIMP-2 with MMP-2 in vivo. Phosphomimetic mutation at TIMP-2 Tyr 90E results in a strong interaction with the active form of MMP-2 and acts as a gain-of-function mutation, as it is more effective in inhibiting MMP-2 catalytic activity. Mechanistic studies in human HT1080 fibrosarcoma cells demonstrate that treatment with anti-c-Src antibodies impaired TIMP-2 phosphorylation, inhibited TIMP-2 interaction with MMP-2 as well as proenzyme (proMMP-2) activation. Conversely, addition of non-phosphorylatable purified TIMP-2 Tyr 90F in HT1080 cell media failed to assist in efficient conversion of pro-MMP-2 to a catalytically active form. Together, the results show extracellular c-Src mediated TIMP-2 phosphorylation to be important and essential in TIMP-2 dual function of promoting MMP activation and inhibiting MMP enzymatic activity, mechanisms that regulate physiological extracellular matrix remodelling and pathological proteolysis.

The present disclosure provides compositions and methods for modulating the activity of extracellular MMP-2. The modulation of MMP-2 activity may be enhancement or may be inhibition. In one embodiment, the modulation (increase or decrease) of MMP-2 activity is achieved by modulation of the extracellular TIMP-2:MMP-2 interaction. For example, the extracellular TIMP-2:MMP-2 interaction may be modulated by using mutant TIMP-2 polypeptide sequences and/or by modulating the activity of extracellular c-Src.

In one aspect, this disclosure provides a method for inhibition of extracellular MMP-2 activity comprising contacting extracellular MMP-2 with a modified TIMP-2, wherein the modification on TIMP-2 comprises replacing one or more tyrosines at positions 62, 90 and 165 with a non-phosphorylatable mimic of tyrosine or with a phosphomimetic of tyrosine, or a combination thereof.

In one embodiment, the method for inhibition of extracellular MMP-2 activity can comprise contacting extracellular MMP-2 with a composition comprising: i) one or more TIMP-2 mutants, wherein one or more tyrosines at or corresponding to positions 62, 90 and 165 have been substituted with Glu (E), Asp (D), Phe (F) or Ala (A), and/or ii) one or more anti-c-Src antibodies.

In one embodiment, the method for inhibition of extracellular MMP-2 activity can comprise inhibiting TIMP-2 phosphorylating activity of extracellular c-Src. For example, the method can comprise contacting extracellular c-Src with anti-c-Src antibodies.

In one aspect, the present disclosure provides compositions and methods for increasing or decreasing the extracellular phosphorylation of TIMP-2 that result in modulating MMP-2 activity. In one embodiment, c-Src, which may be modified to prevent cellular uptake, is introduced or administered to an extracellular environment or region containing or potentially containing TIMP-2 to increase the rate at which extracellular TIMP-2 is phosphorylated or the amount of extracellular TIMP-2 that is phosphorylated. In one embodiment, an antibody to c-Src is introduced or administered to an extracellular environment or region containing or potentially containing TIMP-2 to interfere with the extracellular phosphorylation of TIMP-2 by c-Src, such as by interfering with or preventing the interaction of extracellular TIMP-2 and c-Src. This modulation of TIMP-2 phosphorylation can, in turn, modulate MMP-2 activity as described herein.

In one embodiment, this disclosure provides a method for inhibition of cell migration or cell invasion. Invasion is a tumor cell property. Migration may also occur in homeostatic mechanisms including in endothelium by endothelial cells or epithelium by epithelial cells or during wound healing, arthritis and other diseases. The method comprises delivering to the area or region where inhibition of cell migration or cell invasion is desired, a composition comprising: i) one or more TIMP-2 mutants, wherein one or more tyrosines at positions 62, 90 and 165 have been substituted with E, D, F or A, and/or ii) one or more anti-c-Src antibodies.

In one embodiment, this disclosure provides a method for inhibition of, or prevention of metastasis in an individual who has a metastatic tumor or is at risk of developing metastatic tumor comprising administering to the individual a composition comprising: i) one or more TIMP-2 mutants, wherein one or more tyrosines at positions 62, 90 and 165 have been substituted with E, D, F or A, and/or ii) one or more anti-c-Src antibodies.

This disclosure provides compositions and methods related to prevention or inhibition of, tumor cell migration, tumor cell invasion, or metastasis including: a method for modulating TIMP-2:MMP-2 interactions by administering c-Src antibody and/or a TIMP-2 mutant; a method for modulating conversion of pro-MMP-2 to active MMP-2 by administering c-Src antibody and/or a TIMP-2 mutant; a method for reducing extracellular phosphorylation of TIMP-2 by administering c-Src antibody and/or a TIMP-2 mutant having one or more of the tyrosines at 62, 90 and 165 replaced by F; and a method for increasing TIMP-2 phosphorylation by administering c-Src, which may be modified to prevent cellular uptake.

In one aspect, this disclosure provides isolated, modified TIMP-2 polypeptides, wherein the modification comprises substituting one or more tyrosines at or corresponding to positions 62, 90 and 165 by a non-phosphorylatable mimic of tyrosine or a phosphomimetic of phosphorylated tyrosine. For example, the substitutions at or corresponding to one or more positions 62, 90 and 165 can independently be glutamic acid (Glu, E) or Aspartic acid (Asp, D), or phenylalanine (Phe, F) or (Ala, A). Modified TIMP-2 polypeptides may be referred to herein as TIMP-2 mutants or TIMP-2 variants.

In one embodiment, this disclosure provides an isolated, mutated TIMP-2 molecule of SEQ ID NO: 1, or having at least 90 or 95% homology thereto, wherein tyrosine at one or more of positions 62, 90 and 165 is mutated. The mutation at each position, independently, is substitution of the tyrosine by an amino acid that is non-phosphorylatable or that is a phosphomimetic of phosphorylated tyrosine. For example, the mutation at one or more positions: 62, 90, and 165, independently, is a change of Y to E or F. Only one position (of 62, 90 and 165) may be substituted, or two or all three may be substituted. When two of the three Ys at 62, 90 and 165 are substituted, then it can be any two of the three.

In one embodiment, this disclosure provides an antibody to c-src, which antibody can act on and inhibit extracellular c-src function. For example, the antibody may be one that is generated against the full length c-Src or a fragment of c-Src. The fragment of c-Src may comprise a contiguous sequence of 15 or more amino acids of the c-Src sequence. The fragment of c-Src may comprise about 15 to 40 amino acids, preferably including amino acids 80 and onwards. For example, the fragment may comprise amino acids 80 to 120. In one embodiment, the fragment of src may comprise amino acids 80 to 110. In one embodiment, the fragment is a 27 mer having the sequence corresponding to SEQ ID NO: 5. The anti-Src antibodies may be monoclonal or polyclonal, or may be any antigen binding fragments thereof, or variants thereof.

In one embodiment, this disclosure provides compositions comprising the TIMP-2 mutants, and/or anti-Src antibodies as described herein, and suitable carriers such as buffers and/or pharmaceutical carriers.

In one embodiment, this disclosure provides a method for inhibiting the activity of extracellular MMP-2 and/or TIMP-2, and/or c-Src in an individual by administration to an individual of a composition comprising one or more TIMP-2 mutants and/or one or more anti-Src antibodies or fragments thereof that inhibit the phosphorylation of TIMP-2 by c-Src.

In one embodiment, this disclosure provides a method for inhibiting tumor cell migration or metastasis in an individual by administration to an individual of a composition comprising one or more TIMP-2 mutants and/or one or more anti-Src antibodies or fragments thereof that inhibit the phosphorylation of TIMP-2 by c-Src.

The present disclosure can also be applied to wound healing/tissue repair and other extracellular matrix remodeling events including branching morphogenesis (mammary development). Additionally, the present disclosure can also be applied to diseases characterized by fibrosis where the extracellular matrix is accumulated mostly because the rate of fibrotic tissue formation exceeds that MMPs rate of proteolysis.

BRIEF DESCRIPTION OF THE FIGURES

FIG. 2. Phosphorylation of TIMP-2 Y90 is required for TIMP-2:MMP-2 interaction. (a) In vitro kinase assay and protein-protein interaction. Recombinant proteins were added in the indicated numerical order followed by pulldown. ■, TIMP-2 bound to Ni-NTA beads then MMP-2 is added. ●, TIMP-2 bound to Ni-NTA beads then c-Src is added. MMP-2 is added to the TIMP-2:c-Src complex. ◆, TIMP-2 bound to Ni-NTA beads then c-Src and ATP are added. MMP-2 is added to the phosphorylated TIMP-2: active c-Src complex. (b) SYF and SYF+c-Src were transfected with indicated TIMP-2 WT and mutants. Pulldown and co-pulldown experiments were performed from CM and immunoblots were followed. (c) TIMP-2 Y90 is key to TIMP-2:MMP-2 interaction. WT, non-phosphorylatable (F) and phosphomimetic (E) TIMP-2 mutants were pulldown from 293H CM. Interaction (co-pulldown) of TIMP-2 proteins with secreted MMP-2 is shown. Data represent three independent experiments. Vec, vector control; WT, wild type. +, presence; –, absence; MMP-2, matrix metalloproteinase 2; TF, triple F mutant; TE, triple E mutant; IB, immunoblot; CM, conditioned media.

FIG. 5. Model for the extracellular phosphorylation of TIMP-2 and significance. TIMP-2 interaction with MMP-2 (active and proform) depends on e-Src mediated TIMP-2 phosphorylation (pTIMP-2). Y90 phosphorylation is required for TIMP-2:MMP-2 complex formation in vivo, whereas, lack of Y90 phosphorylation or anti-c-Src antibody treatment prevents proMMP-2 activation.

FIG. 6. Alignment of human TIMPs protein family and phosphorylation of TIMP-2 Y62, Y90 and Y165 residues. (a) Protein sequence alignment (ClustalW) of all four full length human TIMPs (TIMP-1 to -4). TIMP-1 sequence is SEQ ID NO: 2, TIMP-2 sequence is SEQ ID NO:1, TIMP-3 sequence is SEQ ID NO:3, and TIMP-4 sequence is SEQ ID NO:4. TIMP-2 protein domains (signal peptide, N-terminus and C-terminus), separated with red vertical lines, containing the seven tyrosine residues (Y) in pink colored boxes. Stars (*) indicate conserved amino acid residues. Tyrosines (Y) subjected to phosphorylation are shown in red font. (b) TIMP-2 phosphorylation of transiently transfected double and triple F (Y62F/Y90F/Y165F) mutants. Pulldown experiments from 293H whole cell extracts was followed by immunoblotting with a pan-phosphotyrosine antibody (phos-Tyr, 4G10). (c) Wild type (WT) TIMP-2 or TF were transiently transfected in SYF and SYF+c-Src cells. Proteins were pulldown from cell extracts and immunoblotted as shown. WT, wild type; Vec, vector control, TF or triple F (non-phosphorylatable form of TIMP-2), Y62F/Y90F/Y165F mutant; IB, immunoblot. Data represent three independent experiments.

FIG. 9. Anti-c-Src antibodies block signaling of extracellular c-Src. (a and b) SYF+c-Src CM were pre-treated with anti-c-Src antibodies targeting different domains of the protein (exact region is shown in brackets for (a) and (b)), followed by incubation with exogenous recombinant TIMP-2 (rTIMP-2-His$_6$) and analyzed for TIMP-2 phosphorylation and co-pulldown experiments. Independent experiments were performed two or three times.

Figure 1:
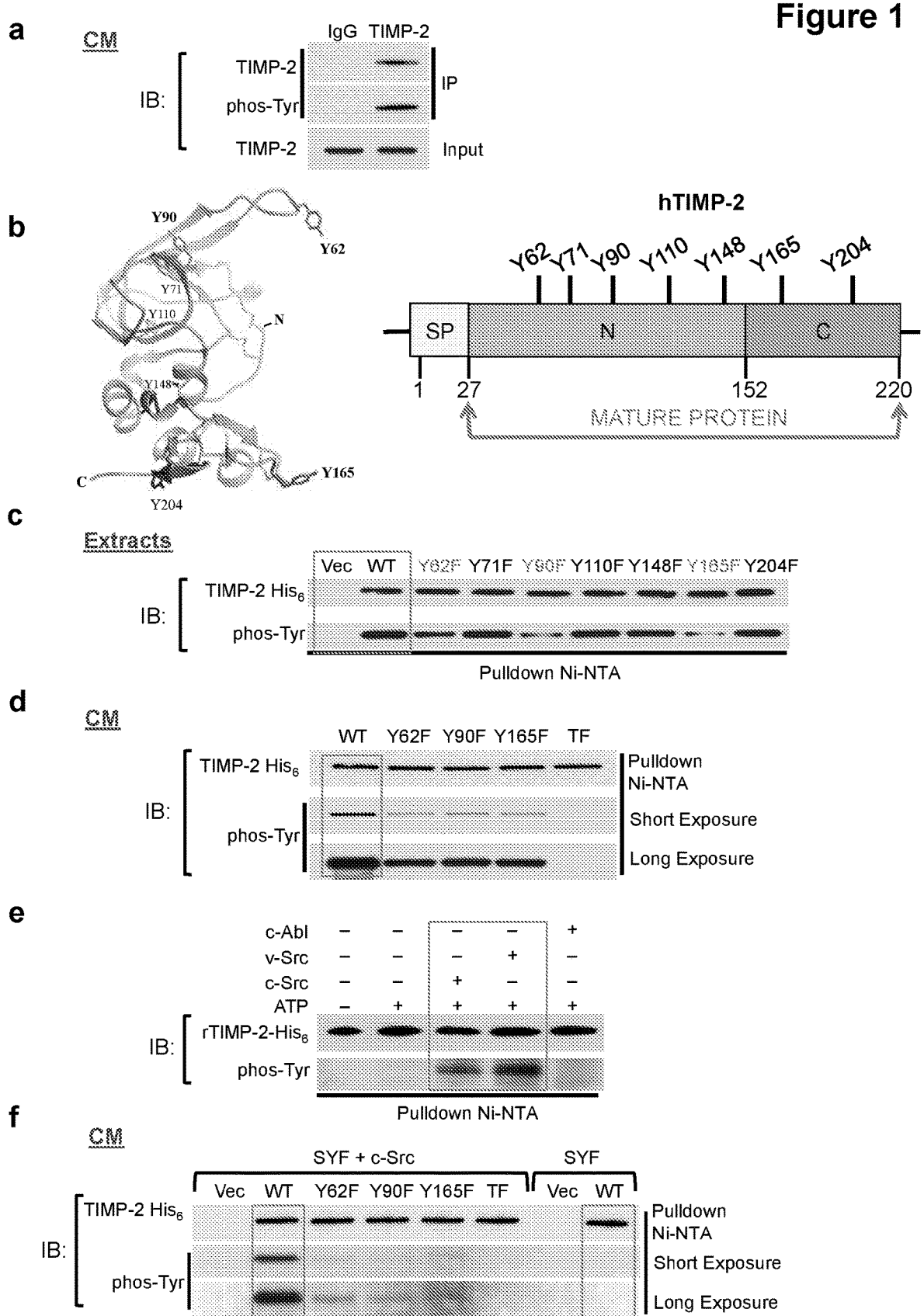
FIG. 1. c-Src tyrosine kinase phosphorylates human TIMP-2 in vitro and in vivo. (a) Endogenous TIMP-2 is tyrosine phosphorylated. TIMP-2 or (IgG control) was immunoprecipitated from HT1080 CM, followed by immunoblotting (IB) as indicated. (b) Human TIMP-2 3D (left) and linear domain (right) structures. TIMP-2 seven tyrosine residues (Y), N-terminal and the C-terminal domains are shown. Tyrosine residues are numbered based on the full-length protein sequence (aa 1-220). (c and d) TIMP-2 $His_6$-tagged WT and mutants were transiently expressed in 293H cells, pulldown from cells (C) or CM (D) and immunoblotted as indicated. (e) c- and v-Src kinases phosphorylate purified recombinant TIMP-2 (rTIMP-2-$His_6$). In vitro kinase assays were performed followed by TIMP-2-$His_6$ pulldown and immunoblotting. (f) TIMP-2 is phosphorylated in the presence of c-Src. Indicated TIMP-2 constructs were transiently expressed in SYF and SYF+c-Src cells, pulldown from CM and immunoblotted. Data represent three independent experiments. SP, signal peptide; Vec, vector control; Y, tyrosine; F, phenylalanine; WT, wild type; phos-Tyr, pan-phosphotyrosine antibody (4G10); TF (TIMP-2 Y62F/Y90F/Y165F); +, presence; –, absence.

FIG. 11. Additional Anti-c-Src antibody to specific domains of src block signaling of extracellular c-Src. (a) CM were pre-treated with anti-c-Src antibody against amino acid (84-110), followed by incubation with exogenous recombinant TIMP-2 (rTIMP-2-His$_6$) and analyzed for TIMP-2 phosphorylation and co-pulldown experiments. Serum starved HT080 cells were incubated with anti-c-Src (84-110) in (b) or with mAb6 antibody in (c) at the indicated concentrations for one hour prior to treatment with TIMP-2 for 16 hours at 37° C.

DETAILED DESCRIPTION OF THE DISCLOSURE

The present disclosure provides compositions that are useful for modulation of extracellular MMP-2 activity. MMP-2 activity may be modulated by interfering with the interaction of MMP-2 with TIMP-2, and/or by inhibiting the phosphorylation of TIMP-2 by extracellular c-Src, and/or by inhibiting the activation of proMMP-2, and/or by interfering with the phosphorylating activity of extracellular c-Src for TIMP-2. The compositions of the present disclosure can comprise modified TIMP-2 polypeptides and/or inhibitors of extracellular c-Src, such as antibodies to c-Src.

By the term "Extracellular TIMP-2" is meant that the TIMP-2 is present in the extracellular region or space, is free of direct contact with a cell or is in direct contact with or bound to an outer cell surface, and is accessible and functional in the extracellular region or space.

By the term "Extracellular MMP-2" is meant that the MMP-2 is present in the extracellular region or space, is free of direct contact with a cell or is in direct contact with or bound to an outer cell surface, and is accessible and functional in the extracellular region or space.

By the term "Extracellular Src" is meant that the Src is present in the extracellular region or space and is accessible and functional in the extracellular region or space.

The term "effective amount" as used herein refers to an amount of an agent sufficient to achieve, in a single or multiple doses, the intended purpose of the step. The exact amount desired or required will vary depending on the particular compound or composition used, its mode of administration, patient specifics and the like. Appropriate effective amount can be determined by one of ordinary skill in the art informed by the instant disclosure using only routine experimentation.

In one aspect, the present disclosure provides a method for inhibiting one or more of the following: activation of extracellular pro-MMP-2, phosphorylation of extracellular TIMP-2, interaction of TIMP-2 with MMP-2, or activity of MMP-2 comprising delivering to an extracellular region in a tissue, an effective amount of one or more modified TIMP-2s and/or one or more inhibitors of extracellular c-Src. The tissue may be in an individual.

In one aspect, the present disclosure provides method for inhibiting one or more of the following: remodeling of extracellular matrix, tumor cell invasion, or cell migration comprising delivering to an extracellular region in a tissue in an individual an effective amount of a composition comprising one or more modified TIMP-2 polypeptides, and/or one or more anti-c-Src antibodies.

In one aspect, the present disclosure provides method for inhibiting or preventing metastasis in individuals who are afflicted with, or who are at risk of, developing metastatic tumors comprising administering to the individual a therapeutically effective amount of a composition comprising one or more modified TIMP-2 polypeptides, and/or one or more anti-c-Src antibodies.

The sequence of human TIMP-2 is provided below.

(SEQ ID NO: 1)
MGAAARTLRLALGLLLLATLLRPADACSCSPVHPQQAFCNADVVIRAKAV

SEKEVDSGNDIYGNPIKRIQYEIKQIKMFKGPEKDIEFIYTAPSSAVCGV

SLDVGGKKEYLIAGKAEGDGKMHITLCDFIVPWDTLSTTQKKSLNHRYQM

GCECKITRCPMIPCYISSPDECLWMDWVTEKNINGHQAKFFACIKRSDGS

CAWYRGAAPPKQEFLDIEDP
(GenBank accession no. NP_003246)

In one aspect, the present disclosure provides isolated, modified TIMP-2 polypeptides, wherein the modification is a change of Y at one or more of positions 62, 90 and 165 to a tyrosine phosphomimetic or to a non-phosphorylatable mimic of phosphorylated tyrosine. For example, a tyrosine phosphomimetic is glutamic acid or aspartate (Asp, D) and a non-phosphorylatable mimic of tyrosine is phenylalanine or alanine (Ala, A). In any modified TIMP-2 polypeptide, D can be substituted for E and A can be substituted for F at positions 62, 90 and/or 165.

In one aspect, the present disclosure includes all polypeptides having at least an 80% homology with the sequence of SEQ ID NO:1, wherein Y at one or more of positions at or corresponding to 62, 90, and 165 is changed to E or F. For example, the polypeptide may have 85, 90, 91, 92, 93, 94, 95, 96, 97, 98, and 99% homology with the sequence of SEQ ID NO:1, wherein Y at one or more of positions at or corresponding to 62, 90, and 165 is changed to E or F. The variations in the extent of homology to SEQ ID NO: 1 may arise from conservative amino acid substitutions, at positions other than at or corresponding to 62, 90 and 165, that are based generally on the relative similarity of R-group substituents and that do not affect the activity or function of TIMP-2. Non-limiting examples of such substitutions contemplated include: gly or ser for ala; lys for arg; gln or his for asn; glu for asp; ser for cys; asn for gln; asp for glu; ala for gly; asn or gln for his; leu or val for ile; ile or val for leu; and arg for lys.

The following are examples of modified TIMP-2 polypeptides. Whenever a position number is mentioned (such as with respect to SEQ ID NO: 1), it is intended to include a position corresponding to that position number if the length of the peptide is different than in the referenced sequence.

A TIMP-2 polypeptide of SEQ ID NO: 1 or a polypeptide having at least 90%, or at least 95% homology thereto, wherein Y at position 90 is changed to E, and Y at positions 62 and 165 are unchanged.

A TIMP-2 polypeptide of SEQ ID NO:1 or a polypeptide having at least 90%, or at least 95% homology thereto, wherein Y at position 90 is changed to F, and Y at positions 62 and 165 are unchanged.

A TIMP-2 polypeptide of SEQ ID NO: 1 or a polypeptide having at least 90%, or at least 95% homology thereto, wherein Y at position 90 is changed to E, and Y at position 62 is changed to E or F, and Y at position 165 is unchanged.

A TIMP-2 polypeptide of SEQ ID NO: 1 or a polypeptide having at least 90%, or at least 95% homology thereto, wherein Y at position 90 is changed to E, and Y at position 165 is changed to E or F, and Y at position 62 is unchanged.

A TIMP-2 polypeptide of SEQ ID NO: 1 or a polypeptide having at least 90%, or at least 95% homology thereto, wherein Y at position 90 is changed to F, and Y at position 165 is changed to E or F, and Y at position 62 is unchanged.

A TIMP-2 polypeptide of SEQ ID NO: 1 or a polypeptide having at least 90%, or at least 95% homology thereto, wherein Y at position 90 is changed to F, and Y at position 62 is changed to E or F, and Y at position 165 is unchanged.

A TIMP-2 polypeptide of SEQ ID NO: 1 or a polypeptide having at least 90% or at least 95% homology thereto, wherein Y at position 90 is changed to E, and Y at positions 62 and 165 are changed to E or F.

A TIMP-2 polypeptide of SEQ ID NO: 1 or a polypeptide having at least 90%, or at least 95% homology thereto, wherein Y at position 90 is changed to F, and Y at positions 62 and 165 are changed to E or F.

A TIMP-2 polypeptide of SEQ ID NO: 1 or a polypeptide having at least 90%, or at least 95% homology thereto, wherein Y at positions 62, 90 and 165 are all changed to E or are all changed to F.

A TIMP-2 polypeptide of SEQ ID NO: 1 or a polypeptide having at least 90%, or at least 95% homology thereto, wherein Y at position 62 is E or F, and Y at positions 90 and 165 are unchanged.

A TIMP-2 polypeptide of SEQ ID NO: 1 or a polypeptide having at least 90%, or at least 95% homology thereto, wherein Y at position 165 is E or F, and Y at positions 62 and 90 are unchanged.

A TIMP-2 polypeptide of SEQ ID NO: 1 or a polypeptide having at least 90%, or at least 95% homology thereto, wherein Y at position 62 is E or F, Y at position 165 is E or F, and Y at position 90 is unchanged.

Variants of the above TIMP-2 mutants may be made where in any of the above mutants, Y at one or more positions at 62, 90 or 165, is/are replaced with a D (Asp) instead of E (Glu), and/or Y at one or more positions at 62, 90 or 165 is/are replaced with an A (Ala) instead of F (Phe). Variants of the TIMP-2 mutants may be made where Ys at one or more positions at 62, 90 and 165 are independently replaced with E, D, F or A.

Modifications of TIMP-2 polypeptides can be made using prokaryotic or eukaryotic expression systems. For recombinant production of proteins comprising or consisting of a TIMP-2 variant as described herein, in general, any polynucleotide encoding the TIMP-2 variant can be provided in an expression vector. "Expression vector" refers to a vector comprising protein expression control sequences operably linked to the TIMP-2 coding sequence. The expression vector can comprise cis-acting elements for expression, including but not limited to promoter elements, enhancer elements, origins of replication, selectable markers, transcription initiation sites, sequences that encode translation initiation sites, and any other sequence that is desirable for protein expression, depending on the expression system chosen. Suitable protein expression vectors which can be designed to express any polynucleotide sequence encoding TIMP-2 variant include all those known in the art, examples of which include but are not limited to cosmids, plasmids and virus-based systems that can incorporate the recombinant polynucleotide encoding the TIMP-2 variants. The system used to express the recombinant TIMP-2 variant proteins of the disclosure can be any suitable organism and include but are not limited to mammalian cell expression systems, insect cell expression systems (e.g., baculovirus-based systems), yeast expression systems, plant cell expression systems, and prokaryotic expression systems.

The anti-Src antibodies of the disclosure may be whole immunoglobulin molecules such as polyclonal or monoclonal antibodies or may be antigen-binding fragments thereof, including but not limited to, Fab, F(ab'), F(ab')2, Fv, dAb, Fd, single-chain antibodies (scFv), bivalent single-chain antibodies, single-chain phage antibodies, diabodies, nanobodies and the like. The fragments of the antibodies may be produced synthetically or by enzymatic or chemical cleavage of intact immunoglobulins or may be genetically engineered by recombinant DNA techniques. These techniques are well known in the art. The antibodies can also be humanized antibodies. The antibody may be a single-domain antibody, which can be obtained by immunization of dromedaries, camels, llamas, alpacas or sharks with the desired antigen and subsequent isolation of the mRNA coding for heavy-chain antibodies. By reverse transcription and polymerase chain reaction, a gene library of single-domain antibodies containing several million clones is produced. Screening techniques like phage display and ribosome display help to identify the clones binding the antigen.

Figure 10:
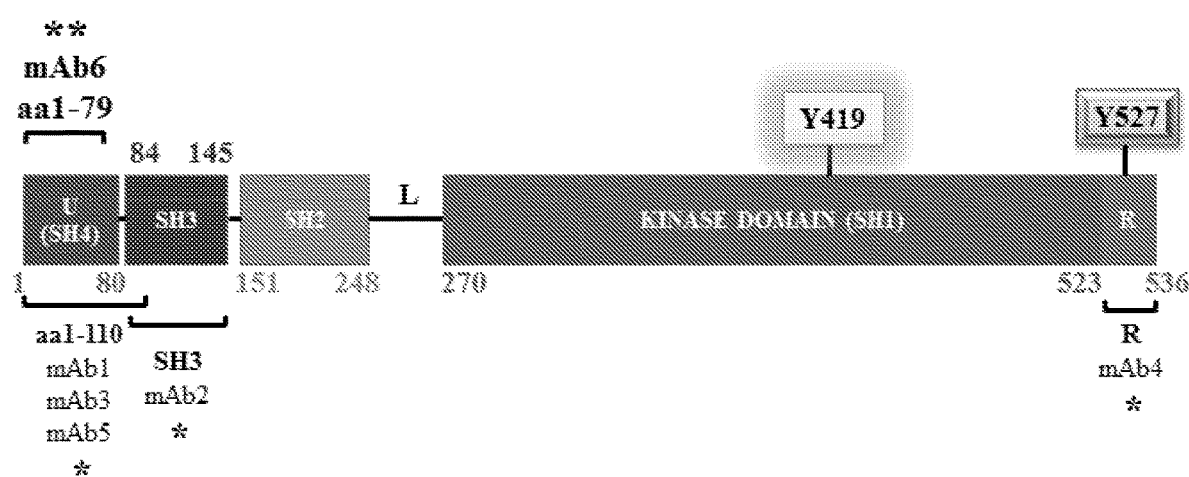
FIG. 10. Representation of human c-Src domain structure and epitopes targeted by selected anti-c-Src antibodies. * indicates antibodies that inhibited phosphorylation of TIMP-2, and ** indicates antibodies that did not inhibit phosphorylation of TIMP-2.

The antibodies suitable for the present disclosure are directed to, or raised against, an epitope of c-Src in the regions designated as SH1, SH2, SH3 or R (FIG. 10). The epitope may overlap these regions. The sequence of human c-Src protein can be found under accession number: UniprotKB-P12931 (SRC_HUMAN). Any epitope (generally of 15 amino acids or more) in the region of amino acids from 80 to 536 of c-Src may be used. For example, an antibody generated against a fragment of c-Src (27 mer, amino acids 84 to 110) can be used. The sequence of this fragment is GGVTTFVALYDYESRTETDLSFKKGER (SEQ ID NO:5). Of the antibodies we tested, we identified only one that does not interfere with the phosphorylation and interaction with MMP-2. The epitope/immunogen of c-Src used for the antibody that did not interfere with phosphorylation of TIMP-2 and its interaction with MMP-2 covers aa 1-79. However, the antibodies targeting the aa 1-110 did inhibit phosphorylation and interaction with MMP-2. Further, there is a ~30 amino acid long peptide of c-Src that seems to be important for the binding of TIMP-2 to c-SRC (aa 80-100 c-Src sequence) and therefore for its subsequent phosphorylation. Thus, in one embodiment, the antibody to c-Src is directed to amino acids 80-100 or 80-110, or to any immunogenic peptide that comprises a sequence corresponding to a portion of the sequence from 80-536.

The antibodies of the present disclosure may be obtained from a human or a non-human animal. In many mammals, intact immunoglobulins have two heavy chains and two light chains. Each of the light chains is covalently linked to a heavy chain by a disulfide bond. The two heavy chains are linked to each other by additional disulfide bonds. The light chain typically has one variable domain (VL) and one constant domain (CL). The heavy chain can also have one variable domain (VH). The variable domains contain complementarity-determining regions (CDRs). The heavy chain can further have three or four constant domains (CH1, CH2, CH3 and CH4). The variability of the constant domains results is various isotypes such as IgA, IgD, IgE, IgG, and IgM.

The antibodies of the present disclosure may be chimeric or humanized antibodies. In a chimeric antibody, portions of the heavy and/or light chains may be identical or homologous to sequences from a particular species while other portions may be identical or homologous to sequences from a different species. A humanized antibody is typically a human antibody that has one or more amino acid residues imported into it (i.e., introduced into it) from a source that is non-human. For example, a humanized antibody is a recombinant protein in which the CDRs of an antibody from a species such as rodent, rabbit, dog, goat, or horse are imported into human heavy and light variable domains. The constant domains of the antibody molecule are generally the same as those of a human antibody.

Antibody fragments can be produced by enzymatic digestion. For example, papain digestion of antibodies produces two identical antigen-binding fragments, called "Fab" fragments, and a "Fc" fragment. The Fab fragment contains an entire L chain and the variable region domain of the H chain (VH), and the first constant domain of one heavy chain. Each Fab fragment is monovalent with respect to antigen binding, i.e., it has a single antigen-binding site. Pepsin treatment of an antibody yields a single large F(ab')2 fragment that roughly corresponds to two disulfide linked Fab fragments having divalent antigen-binding activity and is capable of cross-linking antigen. "Fv" is the minimum antibody fragment that contains a complete antigen-recognition and -binding site and single-chain Fv also abbreviated as "sFv" or "scFv" are antibody fragments that comprise the VH and VL antibody domains connected into a single polypeptide chain. The term "diabodies" refers to small antibody fragments prepared by constructing sFv fragments with short linkers between the VH and VL domains such that inter-chain but not intra-chain pairing of the V domains is achieved, resulting in a bivalent fragment, i.e., fragment having two antigen-binding sites. A single domain antibody (sdAb) is an antibody fragment which has a single monomeric variable antibody domain. ScAbs can be made from heavy-chain antibodies found in camelids.

In one aspect, the present disclosure provides compositions comprising one or more of the TIMP-2 mutants or variants thereof disclosed herein, and/or one or more of the anti-Src antibodies disclosed herein. The compositions may comprise the TIMP-2 mutants or variants thereof and/or anti-Src antibodies in suitable buffers. Different TIMP-2 mutants may be used to provide synergistic effect on inhibition of the TIMP-2-MMP-2 interaction and subsequent MMP-2 activation. Similarly, an anti-Src antibody may be used by itself or with other anti-Src antibodies to provide synergistic effect on the inhibition of TIMP-2-MMP-2 interaction and subsequent MMP-2 activation. The TIMP-2 mutants and the anti-Src antibodies may be used together to provide synergistic effect on the inhibition of TIMP-2-MMP-2 interaction and subsequent MMP-2 activation.

In one embodiment, the composition comprises: i) a modified TIMP-2 polypeptide of SEQ ID NO: 1 wherein Y at position 90 is changed to E, and ii) an anti-Src antibody. In one embodiment, the composition comprises: i) a modified TIMP-2 polypeptide of SEQ ID NO:1 wherein Y at position 90 is changed to E, and ii) an anti-Src antibody that is generated against a peptide of SEQ ID NO:5 (corresponding to amino acids 84-110 of c-Src) or a peptide of smaller length within the sequence of SEQ ID NO:5 (i.e., from amino acids 84 to 110).

In one embodiment, the composition comprises: i) a modified TIMP-2 polypeptide of SEQ ID NO: 1 wherein Y at position 90 is changed to F, and ii) an anti-Src antibody. In one embodiment, the composition comprises: i) a modified TIMP-2 polypeptide of SEQ ID NO:1 wherein Y at position 90 is changed to F, and ii) an anti-Src antibody that is generated against a peptide of SEQ ID NO:5 (corresponding to amino acids 84-110 of c-Src) or a peptide of smaller length within the sequence of SEQ ID NO:5 (i.e., from amino acids 84 to 110).

In one embodiment, the composition comprises: i) a modified TIMP-2 polypeptide of SEQ ID NO: 1 wherein Y at position 90 is changed to F, ii) a modified TIMP-2 polypeptide of SEQ ID NO: 1 wherein Y at position 90 is changed to E, and iii) an anti-Src antibody. In one embodiment, the composition comprises: i) a modified TIMP-2 polypeptide of SEQ ID NO:1 wherein Y at position 90 is changed to F, ii) a modified TIMP-2 polypeptide of SEQ ID NO:1 wherein Y at position 90 is changed to E, and iii) an anti-Src antibody that is generated against a peptide of SEQ ID NO:5 (corresponding to amino acids 84-110 of c-Src) or a peptide of smaller length within the sequence of SEQ ID NO:5 (i.e., from amino acids 84 to 110).

The modified TIMP-2 proteins and or the anti-Src antibodies can be provided in pharmaceutical compositions for administration by combining them with any suitable pharmaceutically acceptable carriers, excipients and/or stabilizers. Examples of pharmaceutically acceptable carriers, excipients and stabilizer can be found in *Remington: The Science and Practice of Pharmacy* (2005) 21st Edition, Philadelphia, PA Lippincott Williams & Wilkins. For example, suitable carriers include excipients, or stabilizers which are nontoxic to recipients at the dosages and concentrations employed, and include buffers such as acetate, Tris, phosphate, citrate, and other organic acids; antioxidants including ascorbic acid and methionine; preservatives such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; and/or non-ionic surfactants such as Tween or polyethylene glycol (PEG). The pharmaceutical compositions may comprise other therapeutic agents.

Administration of formulations comprising modified TIMP-2 polypeptides and/or anti-c-Src antibodies as described herein can be carried out using any suitable route of administration known in the art. For example, the compositions comprising anti-c-Src antibodies or fragments thereof, and/or TIMP-2 variants may be administered via intravenous, intramuscular, intraperitoneal, intracerobrospinal, subcutaneous, intra-articular, intrasynovial, oral, topical, or inhalation routes. The compositions may be administered parenterally directly at the target site (such as near or within a tumor) or enterically. The compositions may be introduced as a single administration or as multiple administrations or may be introduced in a continuous manner over a period of time. For example, the administration(s) can be a pre-specified number of administrations or daily, weekly or monthly administrations, which may be continuous or intermittent, as may be clinically needed and/or therapeutically indicated. Administration may be carried out locally at or near the site of the tumor or may be carried out systemically. Extended release formulations may be used. For example, nanoparticles, a collagen sponge or other means may be used to form a composition with modified TIMP-2 polypeptides and/or anti-c-Src antibodies to release the modified TIMP-2 polypeptides and/or anti-c-Src antibodies over an extended period of time (days (2, 3, 4, 5 or 6), weeks (1, 2, 3, 4, 5, 6, 7) or months (2, 3, 4, 5, 6, 8, 12) locally at or near the tumor. Examples of suitable means are known in the art, including any of those used or investigated for the sustained release of BMP-2 and growth hormone. Encapsulation of modified TIMP-2 polypeptides and/or anti-c-Src antibodies in liposomes or micelles or other materials may also be used to create formulations that will release the modified TIMP-2 polypeptides and/or anti-c-Src antibodies over a sustained period of time.

It will be recognized by those of skill in the art that the form and character of the particular dosing regimen employed in the method of the disclosure will be dictated by the route of administration and other well-known variables, such as the size and age of the individual and the stage of the disease. The amount of modified TIMP-2 polypeptides and/or anti-c-Src antibodies and any other active agent to be included in a composition and/or to be used in the method can be determined by those skilled in the art, given the benefit of the present disclosure. Thus, in one embodiment, an effective amount of a composition of the disclosure is administered. An effective amount can be an amount of the composition that reduces metastasis or that prevents metastasis of tumors. Examples of metastatic tumors include tumors in the brain, lung, breast, prostate, colon, pancreas, kidney, head and neck.

Compositions of the disclosure can be administered in conjunction with any conventional treatment regimen, including sequential or simultaneous administration of chemotherapeutic agents, passive immunotherapies, vaccines, adjuvants and the like. Administration of compositions described herein can be combined with treatment modalities including but not limited to chemotherapies, surgical interventions, and radiation therapy which can be performed prior to, concurrently, or subsequent to administration of the present compositions.

A tumor can be identified as metastatic, or likely to become metastatic, by clinical and biochemical immunohistology. For example the determination of the metastatic tumors is done via either plain chest X-Ray (CXR), conventional cross sectional imaging with the computerized tomography (CT) or magnetic resonance imaging (MRI), nuclear scintigraphy via technetium bone scan or positron emission tomography (PET). Use of available biomarkers, either serum or urine, or blood tests, including liver function tests or circulating tumor cells may also point towards metastatic disease. For example, a patient presenting with a renal mass who on further evaluation is found to have pulmonary nodules or liver lesions or areas of uptake in the body skeleton other than joints is presumed to have metastatic renal cell carcinoma. The work up for metastatic disease varies based on the type of primary tumor.

Another way of diagnosing metastatic disease is via biopsy of the lesion in question located outside the suspected primary tumor. Histologic diagnosis in this example would be confirmatory for metastatic disease.

Further, many patients may have aggressive tumors with presumed metastatic disease based on the knowledge of the behavior of the primary tumor even without radiographic, histologic, or serologic evidence at the time of diagnosis. For example, small cell carcinoma of the urinary bladder is presumed to be "micrometastatic" (metastatic without radiographic proof), and is, therefore, treated with aggressive chemotherapy first. Knowledge of the histologic type of the primary tumor, clinical stage, grade, as well as additional immunohistochemical or other biomarkers often point out to those patients with high likelihood of micrometastatic disease, therefore affecting follow up and management.

In cases where increased phosphorylation of extracellular TIMP-2 in an individual is desired, administration of a composition comprising c-Src can be carried out, where c-Src has been modified to reduce or prevent uptake by cells.

If desired, circulating or local levels of MMP-2 or TIMP-2 may be measured prior to administration of therapeutic compositions. For example, the levels of these polypeptides may be determined by immunological detection techniques (such as ELISA) in a biological tissue or fluid sample from the individual.

The compositions and/or methods of the present disclosure can be used on humans and non-human animals. Non-human animals include, but are not limited to, dogs, cats, horses, cows, pigs, goats, sheep, dairy animals and the like.

The compositions of the present disclosure can be used in any application where extracellular matrix is to be modified, such as to inhibit migration of cells and invasion (such as tumor cells) through the matrix. The TIMP-2 mutants can be used in any application where TIMP-2 is contemplated to be used. The anti-Src antibody generated against the 27 mer of SEQ ID NO:5 can be used for any application where an anti-Src antibody is useful, including for therapeutic, diagnostic and investigative purposes.

The disclosure is further described by the following example, which is intended to be and not limiting in any way.

EXAMPLE 1

The following is an example of the present disclosure describing the role of extracellular Src in regulation of TIMP-2:MMP-2 interaction.

Results

Secreted Human TIMP-2 is Phosphorylated on Y62, Y90 and Y165.

To experimentally assess whether TIMP-2 is a phosphoprotein, specifically targeted on tyrosine residues by a kinase, we first determined that secreted endogenous TIMP-2 is tyrosine (Tyr) phosphorylated. We immunoprecipitated (IP) naturally secreted TIMP-2 protein from the serum free conditioned media (CM) of HT1080 fibrosarcoma cells. Using immunoblotting (IB) and an anti-pan-phosphotyrosine antibody (phos-Tyr, 4G10), we show tyrosine phosphorylation of the secreted TIMP-2 (FIG. 1a).

Human TIMP-2 has seven tyrosine residues, five of them in the N-terminus and two in the C-terminus of the protein (FIG. 1b). To determine which tyrosine residue(s) is(are) subject to phosphorylation, we individually mutated each of the seven tyrosine residues to non-phosphorylatable phenylalanine (F)[12]. Wild type (WT) TIMP-2-His$_6$ and phosphorylation-defective single mutants were transiently transfected in HEK293H cells (FIG. 1c). Ni-NTA pulldown experiments were performed, followed by immunoblotting (IB) with anti-phos-Tyr antibody, and confirmed tyrosine phosphorylation of the WT TIMP-2 (FIG. 1c). Mutation of Y62, Y90 and Y165 to phenylalanine individually resulted in reduced tyrosine phosphorylation of TIMP-2 compared to the WT protein. Our data suggest that these three tyrosine residues are subject to phosphorylation in HEK293H cells (FIG. 2c). Protein sequence alignment of the four human TIMPs members reveals that Y62 and Y165 are unique only to TIMP-2 protein (FIG. 6a). To address whether the identified tyrosine residues are the only ones in human TIMP-2 that are targeted for phosphorylation, we simultaneously mutated the three tyrosine sites to phenylalanine, creating the non-phosphorylatable triple-mutant Y62F/Y90F/Y165F (referred to as TF). WT TIMP-2-His$_6$, single and non-phosphorylatable TF TIMP-2 mutants were transiently transfected in HEK293H cells and the secreted proteins were analyzed from the CM of HEK293H cells by Ni-NTA pulldown experiments (FIG. 1d). Similar experiments were also performed with a series of non-phosphorylatable double mutants (Y62F/Y90F, Y90F/Y165F and Y62F/Y165F) (FIG. 6b). We revealed a decrease in tyrosine phosphorylation in single and double mutants and complete lack of phosphorylation in the TF mutant (FIG. 1d and FIG. 6b). Our data suggest that Y62, Y90 and Y165 are the only tyrosine sites on TIMP-2 that are subject to phosphorylation.

c-Src Tyrosine Kinase Phosphorylates TIMP-2 In Vitro and In Vivo.

To identify the tyrosine kinase(s) responsible for the phosphorylation of Y62, Y90 and Y165 in TIMP-2, we searched for sequence motifs surrounding the targeted tyrosine residues. Amino acid isoleucine (I) at n−1 position of TIMP-2 Y62 and Y90, (n+1 for Y165), is a common denominator in peptides recognized by c-Src or c-Abl tyrosine kinases (FIG. 6a). To determine TIMP-2 phosphorylation by either tyrosine kinase, we carried out an in vitro kinase assay using purified recombinant TIMP-2-His$_6$ (rTIMP-2-His$_6$), followed by pulldown experiments and probing with an anti-phos-Tyr antibody. We revealed that c-Src and more intensely the oncogenic v-Src are the only tyrosine kinases amongst those tested able to phosphorylate TIMP-2 (FIG. 1e). Interestingly, we found that the c-Abl kinase is unable to phosphorylate TIMP-2, suggesting that inherent differences in mechanisms of substrate recognition between c-Abl and c-Src may dictate substrate specificity. To additionally confirm that c-Src phosphorylates TIMP-2 in vivo, we utilized a triple kinase (endogenous c-Src, Yes and Fyn deficient) knockout mouse embryonic fibroblast cell line, SYF, and SYF+c-Src cells with wild-type c-Src reintroduced. WT TIMP-2-His$_6$ and mutants Y62F, Y90F, Y165F and TF were transfected into SYF and SYF+c-Src cells (FIG. if and FIG. 6c). CM and extracts were collected for pulldown experiments as described earlier. Our data confirmed tyrosine phosphorylation of WT TIMP-2 in SYF+c-Src, but not in the parental SYF cell line, suggesting and that c-Src is responsible for TIMP-2 phosphorylation (FIG. if and FIG. 6c). Since phosphorylation of Y62F, Y90F, Y165F and double mutants is reduced, and TF lacks phosphorylation in SYF+c-Src CM, our overall findings provide strong evidence for c-Src-mediated phosphorylation of TIMP-2 on these three tyrosine residues.

c-Src Forms a Ternary Complex with TIMP-2:

MMP2 in vitro. We next examined the importance of TIMP-2 tyrosine phosphorylation on TIMP-2:MMP-2 interaction. We took various steps to address this question, and to begin with, we performed in vitro protein-protein interaction studies and assessed how the presence of c-Src kinase affects TIMP-2:MMP-2 complexes (FIG. 2a). Firstly, we demonstrate that purified recombinant MMP-2 and unphosphorylated rTIMP-2 proteins directly interact to form a binary complex (FIG. 2a, ■). These results suggest that, at least in vitro, TIMP-2 phosphorylation is not required for TIMP-2:MMP-2 complex formation. Next, we looked at whether the presence of full-length c-Src tyrosine kinase influences the formation of TIMP-2:MMP-2 complex. To address this point, we attached TIMP-2-His$_6$ to Ni-NTA-agarose followed by the addition of recombinant human c-Src, and showed that c-Src tyrosine kinase directly interacts with TIMP-2 (FIG. 2a, ●). Addition of recombinant MMP-2 to the TIMP-●2:c-Src complex led to the formation of a ternary complex of TIMP-2:c-Src:MMP-2, with MMP-2 displaying affinity to the TIMP-2:c-Src complex similar to that of binding of MMP-2 to TIMP-2 alone (FIG. 2a, ■). These data suggest that c-Src is not required for, and does not increase, TIMP-2:MMP-2 interaction in vitro. However, these experiments were performed in the absence of ATP, and TIMP-2 was not phosphorylated as shown in the TIMP-2 anti-phos-Tyr immunoblots (FIG. 2a, ●). To address if c-Src mediated phosphorylation of TIMP-2 influences the binding of MMP-2 to the TIMP-2:c-Src complex, we repeated our experiment, as before, with an exception of incubating TIMP-2 with c-Src in the presence of ATP, therefore phosphorylating TIMP-2 in vitro (FIG. 2a, ◆). The results confirm earlier findings of TIMP-2 in vitro phosphorylation by c-Src (FIG. 1e), and TIMP-2:c-Src complex formation (FIG. 2a, ●), while the affinity of c-Src to TIMP-2 remained unchanged, suggesting that phosphorylation of TIMP-2 does not enhance TIMP-2:c-Src complex formation. Yet, when MMP-2 was added to the phosphorylated TIMP-2:c-Src complex, MMP-2 binding is dramatically enhanced suggesting that either the active kinase and/or TIMP-2 tyrosine phosphorylation augmented the TIMP-2:c-Src complex binding properties to MMP-2 (FIG. 2a).

Tyrosine Phosphorylation of TIMP-2 Signals its Interaction with MMP2 in Vivo.

Figure 7:
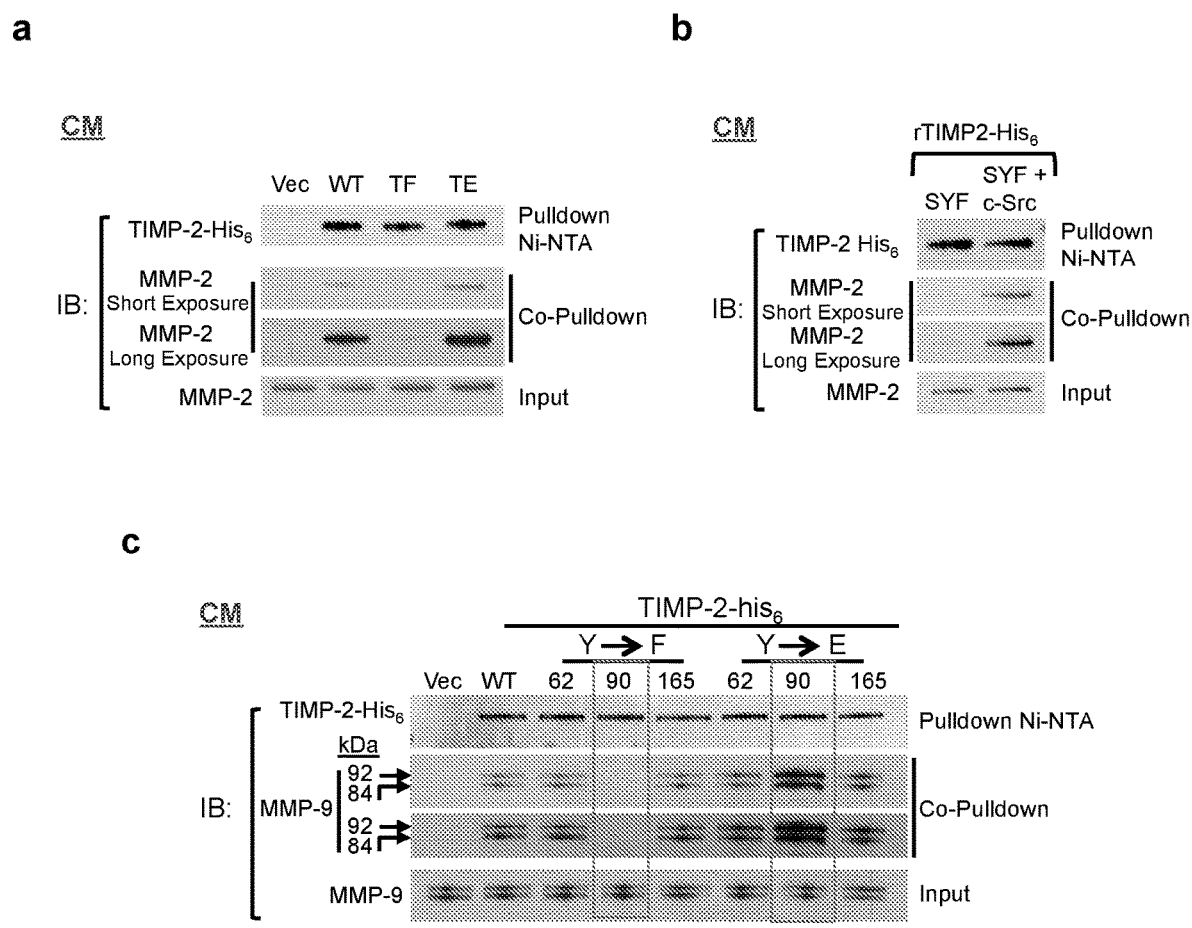
FIG. 7. TIMP-2:MMP-2/-9 interaction depends on TIMP-2 phosphorylation. (a) 293H cells were transiently transfected with WT, TF (Y62F/Y90F/165F) and TE (Y62E/Y90E/Y165E) TIMP-2 mutants. CM were collected for pulldown and co-pulldown experiments and immunoblotted as indicated. (b) SYF and SYF+c-Src cells were treated with equal amounts of exogenous recombinant TIMP-2 and CM were collected. Pulldown, co-pulldown experiments were performed and immunoblotted as indicated. (c) TIMP-2 interaction with endogenous MMP-9 in 293H CM. Cells were transfected with wild type (WT) or indicated mutants and pulldown experiments followed from the CM. MMP-9 92 kDa band corresponds to the proMMP-9 and the 84 kDa band corresponds to the active MMP-9. Vec., vector control; 92 KDa, proMMP-9; 84 KDa, active MMP-9; IB, immunoblot. Data represent three independent experiments.

To address whether c-Src-mediated phosphorylation of TIMP-2 is the reason for the increased binding of MMP-2, we generated a phosphomimetic TIMP-2 mutant Y62E/Y90E/Y165E (referred to as TE), in which each tyrosine is substituted with amino acid glutamic acid (E) to simulate phosphorylation, and determined TIMP-2:MMP-2 interaction in the presence and absence of the kinase (FIG. 2b). WT TIMP-2 and indicated mutants were transiently transfected in SYF and SYF+c-Src cells, followed by pulldown experiments from the CM. Our data show that both non-phosphorylatable and phosphomimetic TIMP-2 proteins (TF and TE) were secreted in the CM of transfected SYF and SYF+c-Src cells. However, in contrast to the results from the in vitro experiments, where TIMP-2 and MMP-2 form a direct complex (FIG. 2a, ■), WT TIMP-2 does not bind to endogenous secreted MMP-2 in SYF CM, resembling the phosphorylation-defective TF (FIG. 2b). This finding is also consistent with WT TIMP-2 lacking tyrosine phosphorylation in SYF CM (FIG. if). Evidently, phosphomimetic TE interacts with MMP-2 in SYF CM, suggesting that, in vivo, TIMP-2 tyrosine phosphorylation signals for TIMP-2: MMP-2 association (FIG. 2b). As anticipated, WT TIMP-2 isolated from the CM of SYF+c-Src and HEK293H cells (treated with exogenous TIMP-2 protein) binds to MMP-2 (FIG. 2b and FIGS. 7a-b). Moreover, TE displays more extensive association with MMP-2 than the WT TIMP-2 indicating that the degree of in vivo tyrosine phosphorylation tightly regulates TIMP-2 interaction with MMP-2. Taken together, our findings strongly suggest that, although rTIMP-2 devoid of any tyrosine phosphorylation can interact with MMP-2 in vitro, tyrosine phosphorylation of TIMP-2 stimulates this interaction in vivo.

Tyr90 Phosphorylation Promotes TIMP-2 Binding to MMP-2 and MMP-9 In Vivo.

We next asked if phosphorylation of a key tyrosine residue promotes TIMP-2 binding to MMP-2. WT TIMP-2-His$_6$, single non-phosphorylatable and phosphomimetic mutants were transfected in HEK293H cells and secreted in the CM. Pulldown experiments revealed that non-phosphorylatable TIMP-2 Y90F is unable to form a complex with MMP-2, whereas, the phosphomimetic Y90E displayed a dominant phenotype and enhanced interaction with MMP-2 compared to the WT protein (FIG. 2c). TIMPs bind non-selectively to MMPs[6] and, therefore, we repeated these experiments, this time looking at the interaction of TIMP-2 and MMP-9 (FIG. 7c). Both MMP-2 and MMP-9 belong to the group of MMPs (the gelatinases) that show substrate specificity primarily to gelatin and type IV collagen. The results obtained from the TIMP-2 pulldown experiments with MMP-9 were similar to those shown earlier from the MMP-2 studies (FIG. 2c and FIG. 7c). Since TIMPs:MMPs complex formation controls extracellular MMP enzyme activity, our data suggest that phosphorylation of TIMP-2 Y90 may act as a signaling switch to regulate MMP-2 (and possibly other MMPs) catalytic activity.

Phosphorylation of TIMP-2 Y90 Enhances its Inhibitory Effect on MMP-2 Catalytic Activity In Vitro.

Figure 3:
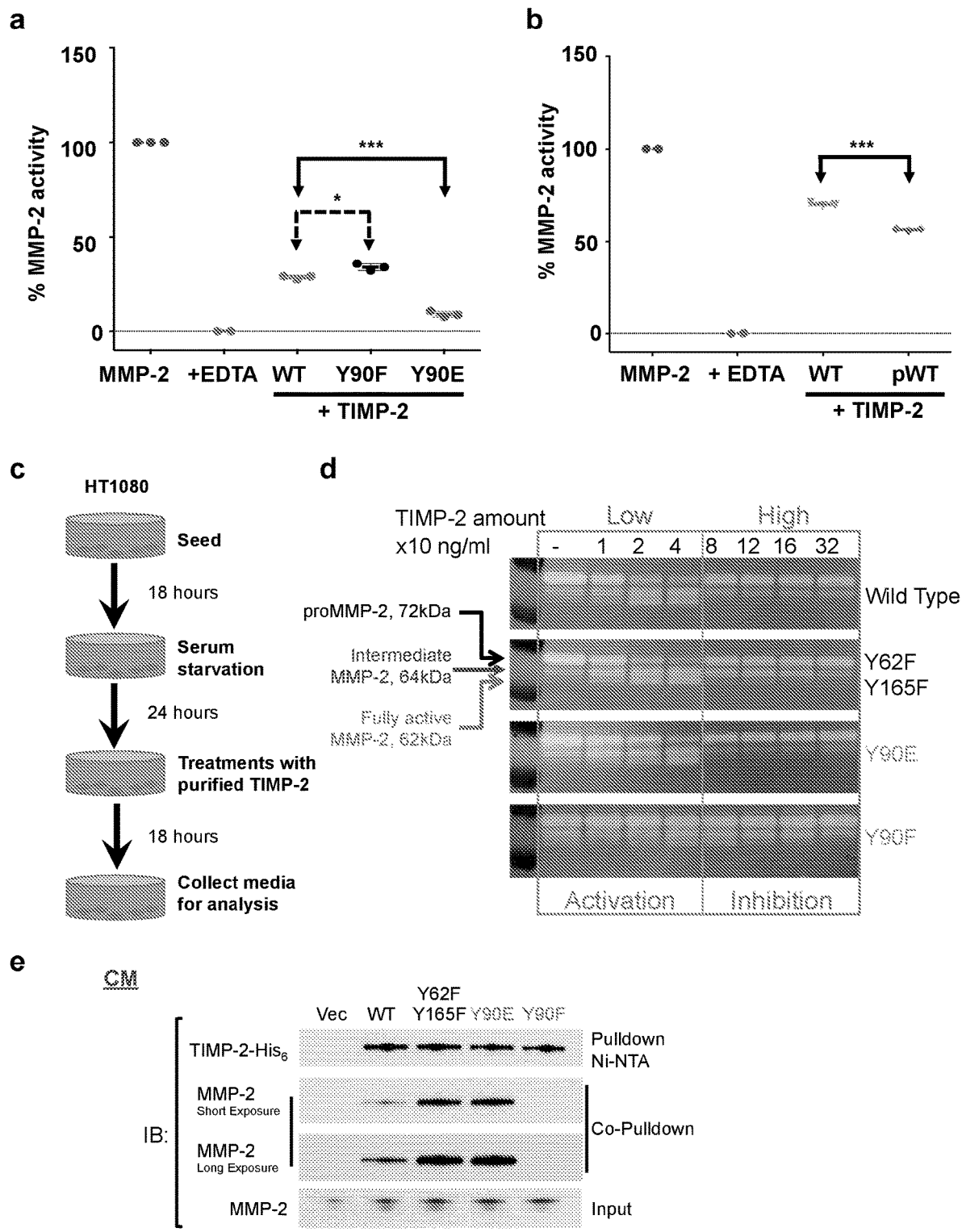
FIG. 3. TIMP-2 Tyr90 regulates MMP-2 enzymatic activity in vitro and proMMP-2 activation in vivo. (a) MMP-2 fluorometric activity assay was performed in the absence and presence of EDTA or purified TIMP-2 WT and mutants Y90F and Y90E. WT TIMP-2 inhibits MMP-2 activity (n=3, mean±s.d., **p<0.0001). TIMP-2 Y90E is more inhibitory, compared to WT TIMP-2 (n=3, mean±s.d., *p=0.0002). TIMP-2 Y90F is less inhibitory, compared to WT TIMP-2 (n=3, mean±s.d., *p=0.02). (b) WT TIMP-2 and in vitro c-Src-phosphorylated WT TIMP-2 (pWT) are shown in the x-axis. WT TIMP-2 inhibits MMP-2 activity (n=3, mean±s.d., **p<0.0001). pTIMP-2 is more inhibitory than the WT TIMP-2 (n=3, mean±s.d.), *p=0.0006). (c and d) TIMP-2 Y90 phosphorylation regulates proMMP-2 activation. Schematic representation of the experimental procedure followed. Gelatin zymography showing the ability of WT TIMP-2 and indicated mutants to mediate activation of proMMP-2 at low amounts (in left rectangle) and inhibit proMMP-2 activation at high amounts (in right rectangle). Proteins were added to the CM of HT1080 cells at the indicated concentrations. (e) MMP-2 and TIMP-2 Y90F mutant do not interact in HT1080 cell CM. Transiently expressed proteins in HT1080 cells were pulldown from CM for interactions experiments. Two Independent experiments were performed using purified proteins from different preparations. RFU, relative fluorescence units. Competitive inhibition of active 62 kDa MMP-2 by different TIMP-2 (wild type and mutants) (f) WT, (g). Y90F, (h). Y90E TIMP-2. Non linear regression. Inhibition constants ($K_i$) were determined from the initial rates. Data were fitted using multiple regression to the classic competitive inhibition equation. Fluorometric activity assays were run in triplicate, varying substrate concentration from 0.83 µM to 6.66 µM. TIMP-2 concentrations for each TIMP-2 form were tested from 0 nM to 2.5 nM. Experiments were performed at least twice. The TIMP-2 WT Ki in (f) 1.5 nM; TIMP-2 90F $K_i$ in (g) is 1.4 nM; TIMP-2 90E $K_i$ in (h) is 0.3 nM, p value=0.02 compared to WT.
Figure 8:
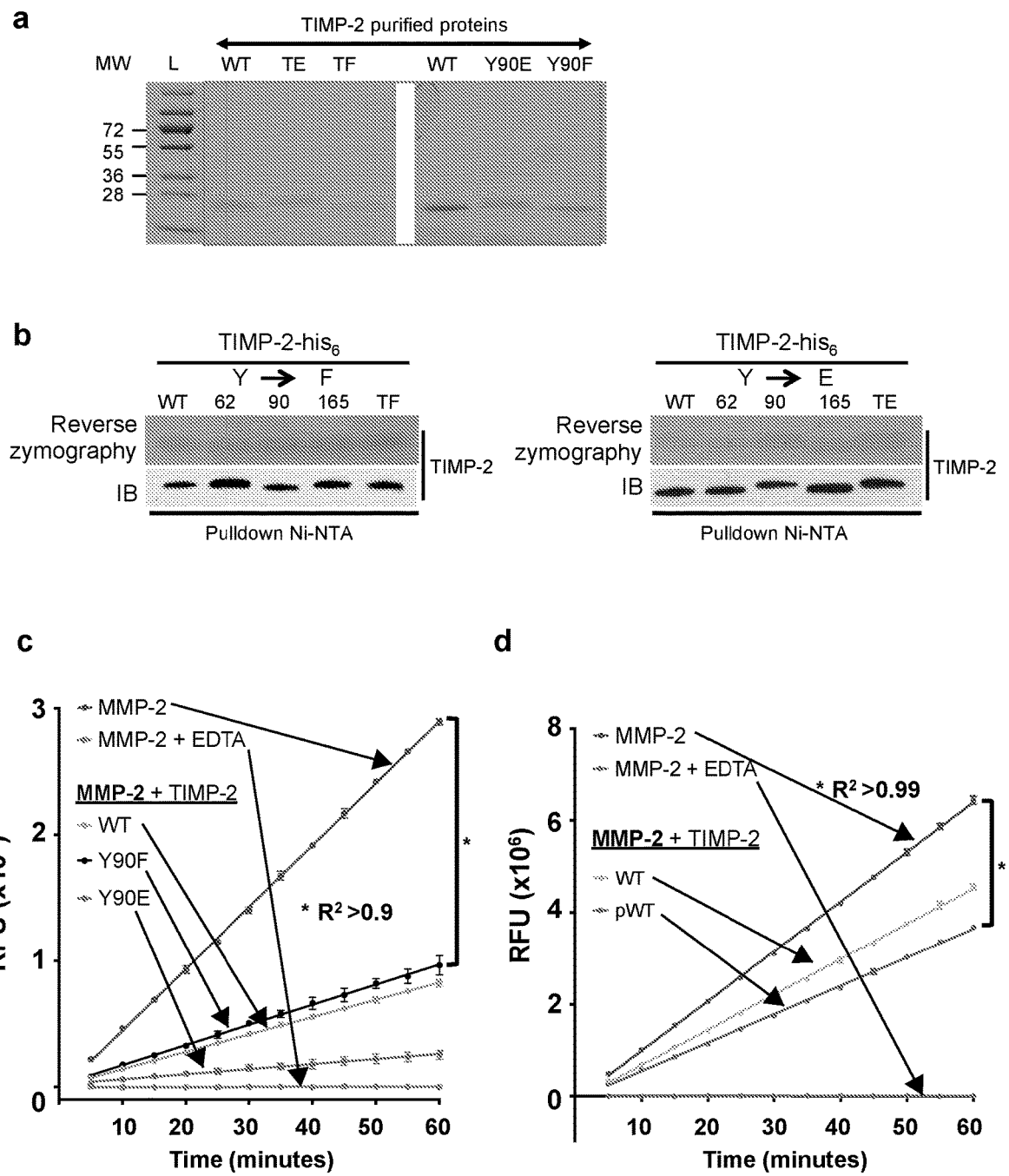
FIG. 8. Characterization of purified TIMP-2 proteins from transiently transfected 293H CM. (a) Purified WT and mutant proteins (TE, TF, Y90E and Y90F) were analyzed for purity in coomassie stained gels (see example enclosed in red rectangle). (b) Purified TIMP-2 proteins (wild type and mutants) from transfected 293H cell media were analyzed for MMP-2 inhibitory activity by reverse zymography. Equal amounts of protein were loaded for western blot (IB). (c) Progress curves of activated MMP-2 kinetic reaction. Fluorometric activity assay for MMP-2 was performed in the absence and presence of indicated TIMP-2 proteins or EDTA. MMP-2 activity assay showing the variables, product accumulation (RFU, y axis) over time (x axis) is performed in the linear phase of the enzymatic reaction for each treatment. All best-fitting lines are straight ($R^2>0.99$) except in the presence of TIMP-2 Y90E ($R^2=0.90$) and EDTA ($R^2=0.1398$) (MMP-2 activity is totally inhibited). (d) Purified WT TIMP-2 and in vitro c-Src-phosphorylated WT TIMP-2 (pWT) shown in the x axis were added to MMP-2. All best-fitting lines are straight (*, $R^2>0.99$) except in the presence of EDTA ($R^2=0.1023$). Error bars are indicative of three technical replicates, showing the standard deviation from the mean. Independent experiments were performed twice. L., ladder; MW, molecular weight; WT, wild type; TE (Y62E/Y90E/Y165E), TF (Y62F/Y90F/Y165F), IB; immunoblot; RFU, relative fluorescence units.

MMPs are known to be released as zymogens and their extracellular enzymatic activities are controlled by interactions with their endogenous protease inhibitors, TIMPs. To address the impact of TIMP-2 Y90 phosphorylation in MMP-2 catalytic activity, we transiently expressed and purified WT TIMP-2-His$_6$ and its phosphotyrosine mutants from HEK293H CM. Purity of the proteins was examined by coomassie blue stain, and equal amounts of purified proteins, as measured by a TIMP-2 ELISA, were analyzed first by immunoblot (IB) and then by reverse zymography to test TIMP-2 ability to inhibit MMP-2-mediated gelatin degradation (FIGS. 8a-b). Our results showed that WT TIMP-2 and the phosphotyrosine mutant proteins are able to directly inhibit MMP-2 proteolytic activity suggesting that these modifications do not affect TIMP-2 ability to inhibit gelatinolysis (FIG. 8b). However, as reverse zymography provides an end-point measurement of enzyme catalytic activity, we next performed real-time quantitative analyses of enzyme kinetics, as a more sensitive method, to measure MMP-2 ability to degrade a fluorogenic peptide substrate (FIG. 3a). From the competitive inhibition assays of active 62 kDa MMP-2 by different TIMP-2s (wild type, and Y90F and Y90E mutants of TIMP-2) (FIGS. 3f, 3g, and 3h), we can conclude using enzyme kinetics quantitative analysis that the potency of inhibition is increased in the TIMP-2 90E phosphomimetic compared to the WT and non-phosphorylatable Y90F (p value=0.02). We also tested recombinant proMMP-2 protein activated in vitro with organomercurial 4-aminophenylmercuric acetate (APMA), prior to testing its catalytic activity (FIG. 3a and FIG. 8c). We showed that WT TIMP-2 and MMP-2 directly interact in vitro (FIG. 2a), therefore, as expected WT TIMP-2 acts as an MMP-2 inhibitor, as does the EDTA chelating agent (FIG. 3a and FIG. 8c). However, phosphomimetic TIMP-2 Y90E inhibitory function correlates with significantly less MMP-2 enzymatic activity suggesting that this mutation exerts a gain-of-function phenotype, whereas, non-phosphorylatable Y90F displayed a slightly less MMP-2 inhibitory activity compared the WT TIMP-2, overall indicating that TIMP-2 Y90E is a more potent enzyme inhibitor (FIG. 3a). To confirm that tyrosine phosphorylation contributes to TIMP-2 inhibitory function, we phosphorylated purified WT TIMP-2 in vitro using active c-Src kinase and then analyzed phosphoTIMP-2 ability to inhibit MMP-2 activity (FIG. 3b and FIG. 8d). Indeed, phosphoTIMP-2 (pWT) is significantly (~25 percent) more inhibitory than the non-phosphorylated WT TIMP-2 toward MMP-2 suggesting that the phosphomimetic Y90E function mimics a WT TIMP-2 protein phosphorylated by c-Src (FIGS. 3a-b).

TIMP-2 Y90 Phosphorylation Regulates proMMP-2 Activation In Vivo.

A TIMP-2 unique function is to assist in the extracellular proMMP-2 activation. The proMMP-2 activation model is complex and involves TIMP-2 behaving as a scaffold between proMMP-2 and a cell membrane-bound MMP (MMP-14), forming a ternary complex that cleaves the MMP-2 proenzyme leading to its activation. To determine the impact of TIMP-2 Y90 phosphorylation in the cellular process of proMMP-2 activation, we treated the highly invasive tumor cell line HT1080 with different amounts of purified WT TIMP-2 protein to stimulate proMMP-2 activation (FIGS. 3c-d). Indeed, at low amounts TIMP-2 activates proMMP-2, shown by the conversion of the MMP-2 72 kDa pro-form to intermediate 64 kDa and fully activated 62 kDa migrated species (FIG. 3d). Likewise, phosphotyrosine mutant proteins TIMP-2 Y62F/Y165F or Y90E assist in zymogen activation. However, non-phosphorylatable TIMP-2 Y90F is unable to promote activation of proMMP-2 suggesting that Y90 phosphorylation is required for in vivo TIMP-2 interaction with and activation of proMMP-2. Pulldown experiments emphasize these findings since Y90F does not bind to MMP-2 in HT1080 CM (FIG. 3e). These data suggest that phosphorylation of TIMP-2 Y90 enhances interaction of TIMP-2 with both active MMP-2 and proMMP-2, that results in reduced proteolytic activity, as well as, increased cellular activation of proMMP-2, respectively.

Secreted c-Src Phosphorylates TIMP-2 in the Extracellular Space.

Recent studies have identified c-Src protein kinases in the extracellular space. Likewise, we first determined that secreted c-Src (referred to as e-Src) is present in the CM derived from cultured mouse and human, normal and tumor cell lines by immunoblotting (IB) (FIGS. 4a-b). We show that mouse (MEF TIMP-2-/-), human immortalized (RWPE1, 293H) and tumor cell lines including fibrosarcoma (HT1080), lung (A549, H460), breast (MCF7) and prostate (RWPE2, LNCaP, DU145, PC3), secrete c-Src at varying levels (FIGS. 4a-b). Absence of cytosolic GAPDH in the CM verifies lack of cytoplasmic fractions in the media. Since secreted c-Src is confirmed outside the cell, we next investigated the ability of e-Src to phosphorylate TIMP-2 extracellularly. We tested this question in both mouse SYF+ c-Src and human fibrosarcoma HT1080 cell lines (FIGS. 4c-e). We added recombinant human TIMP-2 protein (rTIMP-2-His$_6$, devoid of any tyrosine phosphorylation shown earlier in FIGS. 1e and 3a), to SYF+c-Src (or HT1080) CM and demonstrated, first that c-Src is secreted in SYF+c-Src CM (e-Src) and then that rTIMP-2 is tyrosine phosphorylated (FIGS. 4d-e). We also confirmed that phosphorylated TIMP-2 forms a ternary complex with MMP-2 and e-Src in the SYF+c-Src CM, as shown earlier in the in vitro studies (FIGS. 2a and 4d). Considering that c-Src kinase is present in the extracellular space, we next inhibited its function by adding blocking anti-c-Src monoclonal antibodies directly in the CM of SYF+c-Src (or HT1080) cells, and showed that TIMP-2 tyrosine phosphorylation was abolished (FIGS. 4d-e). Similar data were obtained using a variety of anti-c-Src antibodies directed against different kinase epitopes (FIGS. 9a-b). Anti-c-Src antibody treatment abrogates TIMP-2 association with e-Src (FIG. 4c) and MMP-2, possibly due to lack of TIMP-2 tyrosine phosphorylation (FIGS. 4d-e and FIGS. 9a-b). Taken together, our results confirm that blocking extracellular c-Src kinase with anti-c-Src antibodies eliminates extracellular TIMP-2 phosphorylation and interaction with MMP-2.

Blocking Secreted c-Src with Anti-c-Src Antibodies Inhibits proMMP-2 Activation.

We have earlier shown that TIMP-2 phosphorylation is linked to proMMP-2 activation in HT1080 cells (FIGS. 3d-e). We next examined if addition of anti-c-Src antibodies in HT1080 CM could prevent proMMP-2 activation as a result of loss of TIMP-2:MMP-2 interaction. Despite the fact that preservative-free blocking anti-c-Src antibodies, designated specifically for cell-based assays, are currently unavailable, we exploited a biotinylated monoclonal anti-c-Src antibody that, in concentration-dependent manner, demonstrate an inhibitory effect on TIMP-2-assisted proMMP-2 activation in HT1080 CM, as shown by the reduction of the fully active MMP-2 62 kDa at 2 g/ml and absence of 62 kDa species at 10 µg/ml (FIG. 4f). Our data strongly indicate of c-Src-mediated tyrosine phosphorylation of TIMP-2 outside the cells, and without a doubt, it is of immense interest to delineate the exact setting of this process. Strikingly, inhibition of extracellular phosphorylation and protein function with the use of anti-c-Src antibodies establishes a critical relationship between c-Src and extracellular signaling through TIMP-2 phosphorylation.

Discussion

Here, we showed that TIMP-2 is phosphorylated extracellularly by an atypical secreted kinase, c-Src tyrosine kinase. This phosphorylation is required for the in vivo binding of TIMP-2 to MMP-2, since lack or inhibition of phosphorylation prevents TIMP-2:MMP-2 interaction, with remarkable consequences on the proenzyme MMP-2 activation and enzyme activity (FIG. 5). Our data supports that in the extracellular space, protein complexes are dependent upon specific signals, including post-translational modifications, in contrast to the high-affinity protein-protein interactions that readily occur in in vitro systems (FIGS. 2a-c). Structurally, Y62 is located on the tip of the TIMP-2 extended AB loop, a region that displays a large variation in size among different TIMPs. Our current data indicate that Y90 participates in the formation of TIMP-2:MMP-2 and MMP-9 complexes, however, possibly only when it is phosphorylated. Together, our findings describe a potential mechanism by which tyrosine phosphorylation of TIMP-2, and possibly other members of the TIMPs family, could optimize the TIMPs binding interfaces with extracellular interacting proteins, and above all, could increase affinity and specificity to particular MMPs, enhancing complex stability.

The newly described mechanism of MMPs regulation may also have important implications in physiologic or pathologic conditions, where MMPs are key regulators, including matrix remodeling during wound healing, and abnormal extracellular matrix in conditions including cancer, arthritis or cardiovascular diseases. In light of this study's findings, determining the phosphorylated status of TIMP-2 in specific disease states could potentially become a biomarker for response to therapy. Additionally, MMPs inhibitors in the clinic need to be re-evaluated, as poor knowledge of the complexity of MMP regulation has resulted in failed clinical trials. The TIMP-2 mutants described herein can be used for any application where TIMP-2 is currently being used or is contemplated to be used.

Figure 4:
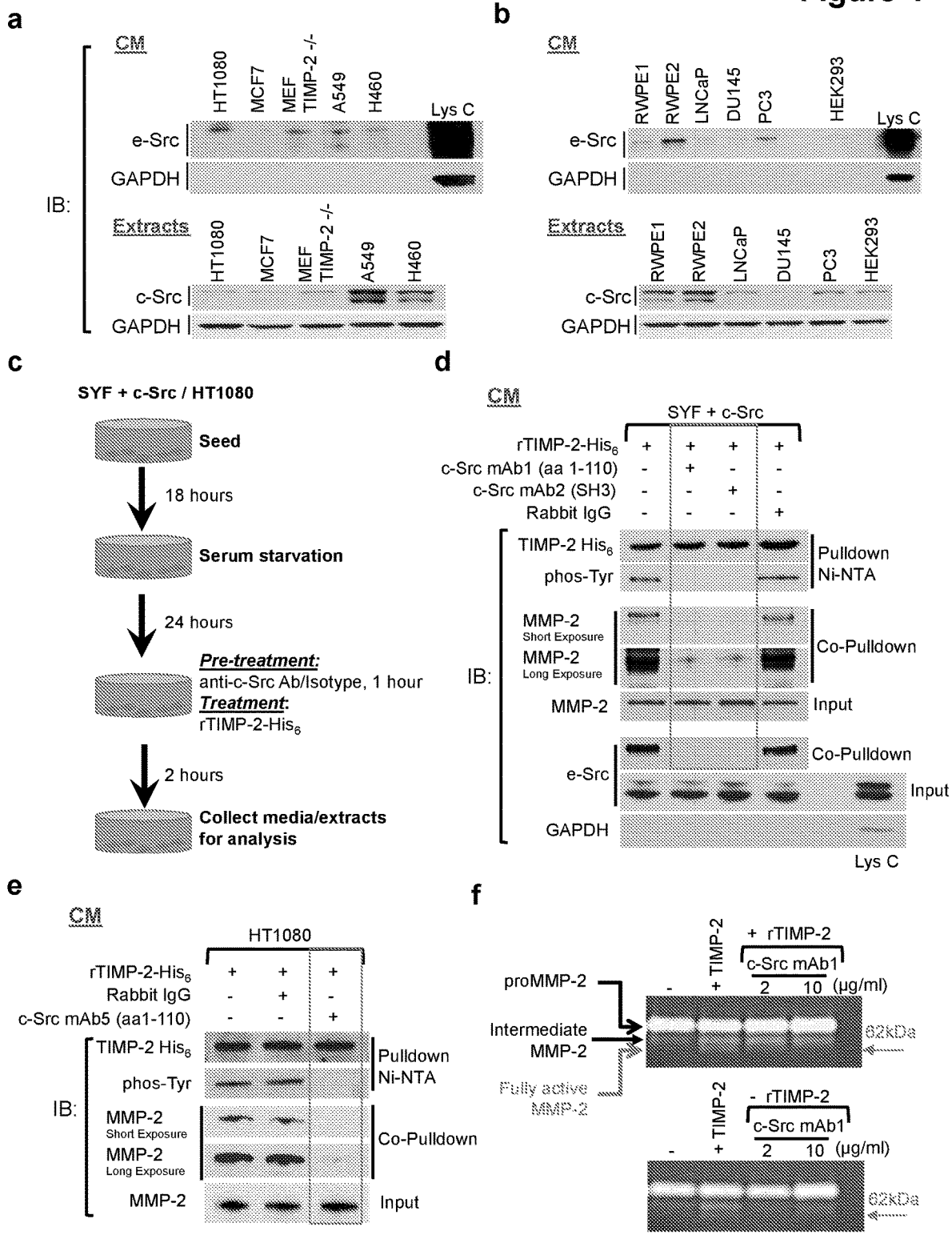
FIG. 4. Secreted c-Src regulates TIMP-2:MMP-2 protein-protein interaction and proMMP-2 activation. (a and b) CM and cell extracts were collected from the following cell lines: mouse TIMP-2−/− ras/myc, immortalized (HEK293H and normal prostate epithelial RWPE1) or tumorigenic derivative RWPE2, human fibrosarcoma HT1080, human breast cancer MCF7, human lung cancer A549 and H460, human prostate tumor cell lines LNCaP, DU145 and PC3. GAPDH indicates equal cellular (extracts) protein content. Absence of GAPDH confirms lack of cytoplasmic fractions in CM. Lys C, is control lysate. (c, d and e) Schematic representation of the procedure followed in experiments described in (d) and (e). Extracellular c-Src (e-Src) regulates TIMP-2:MMP-2 interaction. rTIMP-2-His$_6$ was added in the CM of SYF+c-Src (D) or HT1080 (E) cells after the process of c-Src antibody treatment. c-Src domains targeted by antibodies are shown in brackets. Rabbit IgG is the isotype control treatment. Pulldown and co-pulldown were followed by immunoblotting. GAPDH is present in cell lysates (Lys C). (f) Anti-c-Src antibody treatment inhibits TIMP-2 mediated proMMP-2 activation in HT1080, shown by gelatin zymography. In the absence of TIMP-2, no activation is detected (bottom). CM, conditioned media; Lys C, lysate control.

Finally, we identified extracellular c-Src as the tyrosine kinase that phosphorylates TIMP-2 on three residues. Additionally, our findings indicate that c-Src is secreted in the conditioned media of various human and mouse, normal and cancer cell lines (FIGS. 4a-b). It was surprising that c-Src is released into the extracellular space and that in the amounts released, it performs the function of regulating the interaction of MMP-2 and TIMP-2. Here we show that kinase-specific blocking antibodies succeeded in abolishing TIMP-2 phosphorylation, TIMP-2:MMP-2 interaction and proMMP-2 activation although the secreted c-Src levels (e-Src) seemed relatively low (FIGS. 4, 5 and FIG. 9). Our study opens a new paradigm of extracellular signaling through protein phosphorylation, regulating protein complexes and biological processes outside the cell.

Methods

Cell Culture, Primers, Plasmids, Transfection and Antibodies.

Cell lines were purchased from ATCC and cultured at low passages. No authentication method was used. Experiments were performed in cell cultures maintained up to one month before they were renewed. Cell lines had been tested for *mycoplasma* contamination at the early stages of the experiments. All cultures were analyzed when cells reached up to 70% confluency. 293H, SYF, SYF+c-Src, HT1080, MCF7, MEF TIMP-2-ras/myc, A549 were cultured in DMEM supplemented with 10% fetal bovine serum (FBS) (Invitrogen). RWPE1 and RWPE2 were cultured in Keratinocyte Serum Free Medium (K-SFM) supplemented with 2% FBS (Invitrogen). LNCaP, DU145, PC3 and H460 were cultured in RPMI supplemented with 10% FBS. Wild type TIMP-2 and mutants contained a Six-Histidine ($His_6$) tag at their C-terminus. HEK293H cells (293H) were cultured overnight. The next day they were transfected using TransiT-2020 Reagent (Mirus, #MIR5405) with 2 µg plasmid DNA and manufacturer's protocol. For CM collection, media were replaced with serum free media for an additional 24 hours. Media collected for analysis (see below). Gene synthesis, site-directed mutagenesis and sequence verification were performed by Genewiz and/or using in-house PCR: PfuUltra HotStart (Agilent Technologies) and primers (Eurofins MWG Operon). Mutagenesis primers used in this study are listed in Supplementary Table 2. The following antibodies were used in this study: anti-pan-phosphotyrosine (4G10) (Millipore, #05-1050), anti-6×-His (ThermoFisher Scientific, #MA1-21315), anti-TIMP-2 (Cell Signaling, #5738 and Abcam, ab3161), anti-MMP-2 antibodies (Cell Signaling, #13132 and Millipore, #MAB3308), anti-MMP-9 (Cell Signaling, #3852), anti-GAPDH mAb (Enzo Life Sciences, #ADI-CSA-335-E), anti-c-Src (Cell Signaling, #2109, #2110, #2123), goat anti-mouse IgG-HRP (Santa Cruz Biotechnology Inc., #sc-2005) and goat anti-rabbit IgG-HRP (Santa Cruz Biotechnology Inc., #sc-2004).

Anti-c-Src antibodies for blocking experiments: rabbit anti-Src mAb1 (32G6, biotinylated) (Cell Signaling, #8077), rabbit (DA1E mAb IgG XP™ Isotype control, biotinylated) (Cell Signaling, #4096), mouse anti-Src mAb2 (Clone 327) (Abcam, #ab16885), rabbit IgG (Abcam, #ab172730), mouse anti-Src mAb3 (L4A1) (Cell Signaling, #2110), mouse IgG1, kappa control (Abcam, #ab18437), rabbit anti-Src mAb4 (36D10) (Cell Signaling, #2109), rabbit anti-Src mAb5 (32G6) (Cell Signaling, #2123).

c-Src Antibody Treatments.

In protein-protein interaction studies cells were seeded overnight followed by serum starvation for 24 hours. Different anti-c-Src antibodies or IgG isotype controls were added to the serum free media for 1 hour at 1 µg/ml followed by the addition of purified recombinant TIMP-2-$His_6$ at 50 ng/ml for 2 hours. For proMMP-2 activation and gelatin zymography experiments, HT1080 cells were grown in serum free media for 24 hours followed by treatments with anti-c-Src biotinylated antibody (Cell Signaling) for 2 hours followed by treatment with 293H purified wild type TIMP-2 protein (20 ng/ml) for another 24 hours. This experiment was performed three times using wild type TIMP-2 from the same preparation and twice using TIMP-2 from different preparations. Media collected and analyzed as described (see Gelatin zymography).

Detection of c-Src in Conditioned Media of Normal and Cancer Cell Lines.

Cell lines were cultured and serum starved for 24 hours. Cell extracts and conditioned media were collected and processed as described below. Non-concentrated protein samples from conditioned media were equalized to the cellular protein levels prior to immunoblotting (see below). Analysis was performed using the top band of c-Src immunoblot commonly present in all analyzed samples. Densitometry showing Intensity ratio of c-Src in CM/Total was performed from two repeated experiments using two different antibodies against c-Src.

Immunoblotting.

Conditioned media were obtained after 24 hours of serum starvation and treatments. Cell media were centrifuged at 1000 rpm for 5 minutes to remove any floating cells without lysing them, and supernatant from this step was used in experiments. Cell extracts were obtained by washing confluent cells with ice-cold PBS, lysing with 0.1% NP40 lysis buffer containing protease and phosphatase inhibitors (Roche) (see Supplementary Table 4), and centrifuging at 14000 rpm in a microcentrifuge at 4° C. for 10 min. Protein concentrations of the resulting supernatants were determined using Bradford assay (Bio-Rad). Equal amounts of protein in 5× protein loading buffer were boiled for 5 min, loaded on 4-20% polyacrylamide gradient gels (Bio-Rad), and electrophoresis was performed in denaturing conditions. After transfer to nitrocellulose membranes (Bio-Rad), samples were blocked in TBST (TBS+0.1% Tweenx20) with 5% non-fat dry milk and incubated with primary antibodies at 4° C. overnight. Blots were incubated with the appropriate HRP-conjugated secondary antibodies for 1 hour at room temperature. Bands were visualized by incubating with ECL 2 substrate (Thermo Scientific), followed by different exposures to CLASSIC X-Ray film (Research Products International Corp).

Pulldown Ni-NTA and Immunoprecipitation.

Equal amounts of isolated cell extract proteins were incubated with HisPur Ni-NTA Resin (ThermoScientific) for 2 hours at 4° C. Immunopellets were washed 4 times with fresh lysis buffer (20 mM HEPES pH 7.0, 100 mM NaCl, 1 mM MgCl2, 0.1% NP40, protease inhibitor cocktail (Roche) and PhosSTOP (Roche)). Proteins bound to Ni-NTA agarose were washed with 50 mM imidazole in lysis buffer (20 mM Tris-HCl pH 7.5), 100 mM NaCl, protease inhibitor cocktail and PhosSTOP) and eluted with either 300 mM imidazole in lysis buffer or with 5× Laemmli buffer. Pulldowns were also performed using conditioned media concentrated ~10× using Amicon Ultra 10K centrifugal filters (Millipore) according to the manufacturer's protocol. HiPur Ni-NTA Resin was used to pulldown $His_6$-tagged TIMP-2 from concentrated conditioned media. Briefly, HisPur Ni-NTA Resin was washed 3 times by vortexing resin with 0.1% NP40 lysis buffer and pipetting off supernatant. Concentrated conditioned media was combined with washed HisPur Ni-NTA Resin, and placed on rotator at 4° C. for 1 hour. Wash step was repeated 4 times with 1% NP40 buffer+150 mM NaCl to reduce non-specific binding of proteins to resin. 5× protein loading buffer was added to resin and boiled for 5 minutes. Samples were created from supernatant after removing resin by centrifugation at 15000 rpm for 30 seconds. Precipitated proteins were separated by SDS-PAGE and transferred to nitrocellulose membranes. Precipitated and co-precipitated proteins were detected by immunoblotting with indicated antibodies.

In Vitro Kinase Assays.

Wild type human TIMP-2 was tagged at its C-terminus with $His_6$ in pcDNA3.3 for mammalian expression. TIMP-2 was incubated with 50 µl of Ni-NTA agarose (Qiagen) for 2 hr. The Ni-NTA agarose beads were washed with 30 mM imidazole and then incubated with 50 ng of baculovirus-expressed and purified active cSrc-GST, vSrc-GST and c-Abl (SignalChem) for in vitro kinase assay in the presence or absence of ATP (Sigma). When necessary and after extra washes, recombinant human MMP-2 was added. The assay was carried out in 50 mM Tris-HCl (pH7.5), 10 mM MgCl2 and 0.2 mM ATP, at 28° C. for 15 min. The reaction was quenched by addition of an equal volume of protein loading buffer and immunoblotting was performed in denaturing conditions.

Purification of TIMP-2-$His_6$ Mutants from 293H Conditioned Media.

To purify TIMP-2-$His_6$ mutants, we used 50 times concentrated conditioned media from 293H cells in which the TIMP-2-$His_6$ wild type and mutants had been transiently expressed. Immunoprecipitation protocol was followed as described before until the second wash step. After washing resin 4 times with 1% NP40 buffer+500 mM NaCl, TIMP-2 reconstitution buffer containing 0.5 M imidazole was added to resin and placed on rotator at 4° C. for 1 hour. Samples were centrifuged at 3000 rpm for 30 seconds to release the protein and supernatant was loaded into Amicon Ultra 10K centrifugal filters (EMD Millipore). Resin was washed once with TIMP-2 reconstitution buffer (without imidazole) and this wash was also processed through Amicon Ultra 10K centrifugal filters. Purified TIMP-2-$His_6$ proteins were concentrated down to ~50 µl. For a second round of purification, this fraction was combined with 1% NP40 buffer+500 mM NaCl and placed on rotator at 4° C. for 15 min. Using Amicon Ultra 50K centrifugal filters (Millipore), samples were concentrated down to ~100 µl. Flow-through was kept. Concentrated sample above filter was then washed with 1% NP40 buffer+500 mM NaCl and concentrated down to ~100 µl again. This wash step was repeated 3 times. Combined flow-through was saved and placed in Amicon Ultra 10K centrifugal filters to concentrate the purified TIMP-2-$His_6$ samples and remove salt from buffer. Samples were concentrated down to ~30 µl, and flow-through from this step was discarded. Buffer exchange was done by placing TIMP-2 reconstitution buffer above filter and concentrating again to yield a final volume of ~30 µl. The purity of the isolated proteins was examined by Coomassie staining of SDS-PAGE gels using GelCode Blue Safe Protein Stain (Thermo Scientific). TIMP-2 concentrations were determined using the human TIMP-2 Quantikine ELISA kit (R&D).

Gelatin Zymography.

Gelatinase activity in conditioned media was detected by gelatin zymography. HT1080 cell cultures in 24-hour serum-free media were treated with different concentrations of purified TIMP-2 (wild type or mutants) for another 18 hours. Equal amounts of conditioned media from HT1080 cells with and without treatments were subjected to electrophoresis using 8% acrylamide gels containing 0.1% gelatin. The gels were incubated for 30 min at room temperature in zymogram renaturing buffer (Novex, Invitrogen), 30 min at room temperature in zymogram developing buffer (Novex), and then transferred to fresh zymogram developing buffer for overnight incubation at 37° C. Gels were then stained with Coomassie Brilliant Blue R-250 (Bio-Rad) and briefly destained in 10% acetic acid, 40% methanol and distilled water. They were imaged using an Epson Perfection V700 scanner. Gelatinase activity was detected as transparent bands on a dark background. Recombinant human MMP-2 was run alongside conditioned media to confirm the identity of MMP-2 in the samples. Two independent proMMP-2 activation experiments were performed using proteins prepared from different purifications for treatment.

Reverse Zymography.

Reverse gelatin zymography was performed to test wild type and mutant TIMP-2 proteins MMP-2 inhibitory function. Equal amounts (1 ng) of purified TIMP-2-His$_6$ mutants were run in 15% acrylamide gels containing 0.225% gelatin (Sigma) and 50 ng/ml recombinant MMP-2. The gels were incubated for 2 hours at room temperature in zymogram renaturing buffer, 30 min at room temperature in zymogram developing buffer, and then transferred to fresh zymogram developing buffer for overnight incubation at 37° C. (Invitrogen). Gels were stained and imaged as described in gelatin zymography. TIMP-2 inhibitory activity was detected as dark positive staining bands over a clear background. Recombinant human TIMP-2 (Abcam) was run alongside purified TIMP-2-His$_6$ mutants as a positive control.

MMP-2 Enzymatic Activity Assay.

Enzyme kinetics of MMP-2 in the absence and presence of enzyme inhibitors (EDTA or TIMP-2) were assessed using the SensoLyte 520 MMP-2 Assay kit (AnaSpec). Manufacturer's protocol was followed. Final concentration of constituents used in assay: MMP-2=100 ng/mL, wild type and mutant purified proteins TIMP-2-His$_{6-8}$ ng/mL, EDTA=25 mM. Progress curves were plotted over time. Kinetic readings were taken every five minutes for one hour. Velocities of the reactions were taken at the linear part of the progress curves. Slopes were determined using linear regression at a fixed enzyme and substrate concentration. Values were transformed to percent MMP-2 activity (%). Independent data points from the technical replicates are plotted. Error bars correspond to s.e.m±s.d. from two to three technical replicates. Two experimental replicates using protein purifications from different preparations were performed. Measurements were taken using SpectraMaxi3 (Molecular Devices).

Statistical Analysis.

No statistical methods were used to predetermine sample size. P values for MMP-2 enzymatic activity assay were calculated using unpaired two-tailed Student's t-tests with Welch's correction for unequal SDs when two groups were compared (GraphPad Prism 6). Velocities (RFU/sec) were transformed to per-cent (%) MMP-2 activity. P values with asterix indicate significance. In the experiments, n represents the number of technical replicates. The overall presented experiments in the manuscript are representative of minimum two, generally three biological replicates.

EXAMPLE 2

This example describes the use of an anti-Src polyclonal antibody to inhibit phosphorylation of extracellular TIMP-2 by src. Six commercially available monoclonal antibodies against c-Src (mAb1l-mAb6) were tested for their ability to inhibit tyrosine phosphorylation (Tyr phospho) of TIMP-2 and TIMP-2 interaction with the 72 kDa MMP-2 in the conditioned media (CM). Five out of six, mAb1-mAb5, inhibited TIMP-2 Tyr phospho and its interaction with the 72 kDa MMP-2 in the CM. Three of the five antibodies (mAb1, mAb3 and mAb5) were raised against c-Src amino acids 1-110. We identified only one (mAb6) that does not inhibit Tyr phospho of TIMP-2 and its interaction with 72 kDa MMP-2 in the CM. mAb6 was raised against human c-Src amino acids 1-79 (Unique/SH4 c-Src region).

Thus, we deduce that the c-Src region between amino acids 80-110, i.e the beginning of the c-Src SH3 domain (amino acids 84-145), is important for c-Src:TIMP-2 interaction, 72 kDa MMP2:TIMP-2 interaction, and TIMP-2 Tyr phospho. We therefore, designed a rabbit polyclonal antibody using a 27-mer region (SEQ ID NO:5), c-Src amino acids 84-110 (cSrc pAb (84-110)). We tested the cSrc pAb (84-110) for inhibition of TIMP-2 phosphorylation and TIMP-2 interaction with MMP-2 in HT1080 cells. The data show that the c-Src pAb (aa 84-110) inhibits TIMP-2 Tyr phospho and interaction with 72 kDa MMP-2 protein (FIG. 11a).

We also tested anti-c-Src (84-110) ability to inhibit TIMP-2 mediated 72 kDa MMP-2 activation. We treated serum starved HT080 cells with anti-c-Src (84-110) for one hour prior to treatment with TIMP-2 for 16 hours at 37° C. As shown in FIG. 11b, c-Src antibody blocked the full activation (64 kDa intermediate to 62 kDa fully active) of MMP-2. In contrast, antibody mAb6 did not have such an effect suggesting that the c-Src SH3 region amino acid 84-110 plays an essential role in the activation process of 72 kDa MMP-2 (see below FIG. 1c).

These results support the use of anti-Src antibodies to inhibit TIMP-2 mediated MMP-2 activation, and for limiting tumor cell migration.

While the present invention has been described through various embodiments, it will be apparent to those skilled in the art that routine modifications may be made and such modifications are intended to be within the scope of this disclosure.

What is claimed is:

1. An isolated, mutated TIMP-2 molecule of SEQ ID NO: 1, or having at least 95% homology thereto, wherein the Tyr (Y) corresponding to amino acid position 62 is substituted by Glu (E), the Tyr (Y) corresponding to amino acid position 90 is substituted by Glu (E) or Phe (F), and/or the Tyr (Y) corresponding to amino acid position 165 is substituted by Glu (E) or Phe (F).

2. The isolated, mutated TIMP-2 molecule of claim 1, wherein the Y corresponding to amino acid position 62 is substituted by E.

3. The isolated, mutated TIMP-2 molecule of claim 1, wherein the Y corresponding to amino acid position 165 is substituted by E.

4. The isolated, mutated TIMP-2 molecule of claim 1, wherein the Y corresponding to amino acid position 165 is substituted by F.

5. The isolated, mutated TIMP-2 molecule of claim 1, wherein the Y corresponding to amino acid position 90 is substituted by E.

6. The isolated, mutated TIMP-2 molecule of claim 1, wherein the Y corresponding to amino acid position 90 is substituted by F.

7. The isolated, mutated TIMP-2 molecule of claim 1, wherein the Y corresponding to amino acid positions 62, 90, and 165 are each substituted by E.

8. The isolated, mutated TIMP-2 molecule of claim 1, wherein the Y corresponding to amino acid positions 62, 90, and 165 are each substituted by F.

* * * * *